US011871948B2

(12) United States Patent
Grandfield et al.

(10) Patent No.: US 11,871,948 B2
(45) Date of Patent: Jan. 16, 2024

(54) EMBOLECTOMY DEVICE HAVING MULTIPLE SEMI-TUBULAR CLOT ENGAGING STRUCTURES

(71) Applicants: STRYKER CORPORATION, Kalamazoo, MI (US); STRYKER EUROPEAN HOLDINGS I, LLC, Kalamazoo, MI (US)

(72) Inventors: Ryan M. Grandfield, Livermore, CA (US); Aleksandr Leynov, Walnut Creek, CA (US)

(73) Assignees: Stryker Corporation, Kalamazoo, MI (US); Stryker, European Holdings I, LLC, Kalamazoo, MI (US)

( * ) Notice: Subject to any disclaimer, the term of this patent is extended or adjusted under 35 U.S.C. 154(b) by 337 days.

(21) Appl. No.: 17/461,890

(22) Filed: Aug. 30, 2021

(65) Prior Publication Data

US 2021/0386444 A1    Dec. 16, 2021

Related U.S. Application Data

(63) Continuation of application No. 16/488,121, filed as application No. PCT/US2018/019292 on Feb. 22, 2018, now Pat. No. 11,116,529.

(Continued)

(51) Int. Cl.
*A61B 17/221*    (2006.01)
*A61B 17/22*    (2006.01)

(52) U.S. Cl.
CPC .... *A61B 17/221* (2013.01); *A61B 2017/2215* (2013.01); *A61B 2017/22034* (2013.01)

(58) Field of Classification Search
CPC ............ A61B 17/22031; A61B 17/221; A61B 2017/2215; A61B 2017/22034
See application file for complete search history.

(56) References Cited

U.S. PATENT DOCUMENTS 6,660,021 B1 * 12/2003 Palmer ................... A61F 2/013
606/200
8,529,596 B2    9/2013 Grandfield et al.
(Continued)

FOREIGN PATENT DOCUMENTS

WO    WO2012120490    9/2012
WO    WO2018156813    8/2018

OTHER PUBLICATIONS

PCT International Search Report and Written Opinion dated Apr. 20, 2018 for PCT/US2018/019292, Applicant Stryker Corporation, 10 pages.

*Primary Examiner* — Wade Miles
(74) *Attorney, Agent, or Firm* — Vista IP Law Group, LLP

(57) ABSTRACT

An elongate embolectomy device having a radially constrained configuration and a radially expanded configuration, the embolectomy device being formed out of a plurality of elongate clot engaging structures, each clot engaging structure comprising a plurality of interconnected struts forming an open cell pattern, wherein, when the embolectomy device is in the radially expanded configuration, the clot engaging structures each have a semi-tubular arcuate profile, including a convex face and an concave face facing opposite the convex face, extending along a length of the embolectomy device, the clot engaging structures being longitudinally disposed relative to each other such that the concave faces are facing radially outward, and the convex surfaces are facing radially inward, respectively, relative to a longitudinal axis of the embolectomy device.

20 Claims, 32 Drawing Sheets

Related U.S. Application Data

(60) Provisional application No. 62/463,419, filed on Feb. 24, 2017.

(56) References Cited

U.S. PATENT DOCUMENTS

| | | | |
|---|---|---|---|
| 8,852,205 B2 | 10/2014 | Brady et al. | |
| 11,116,529 B2 * | 9/2021 | Grandfield | A61B 17/221 |
| 2007/0288038 A1 * | 12/2007 | Bimbo | A61B 17/221 |
| | | | 606/127 |
| 2012/5021525 | 8/2012 | Grandfield et al. | |
| 2015/0080937 A1 * | 3/2015 | Davidson | A61F 2/01 |
| | | | 606/200 |
| 2016/0008015 A1 * | 1/2016 | Nguyen | A61B 17/221 |
| | | | 606/127 |
| 2016/0081702 A1 * | 3/2016 | Kan | A61B 17/50 |
| | | | 156/267 |
| 2016/0174996 A1 * | 6/2016 | Martin | A61B 17/32056 |
| | | | 606/127 |
| 2017/0100143 A1 * | 4/2017 | Grandfield | A61B 17/221 |
| 2017/0112512 A1 * | 4/2017 | Davidson | A61B 17/22031 |
| 2018/0064454 A1 * | 3/2018 | Losordo | A61B 17/221 |
| 2018/0140314 A1 * | 5/2018 | Goyal | A61B 17/221 |
| 2020/0085454 A1 * | 3/2020 | Gogoussis | A61B 17/221 |

\* cited by examiner

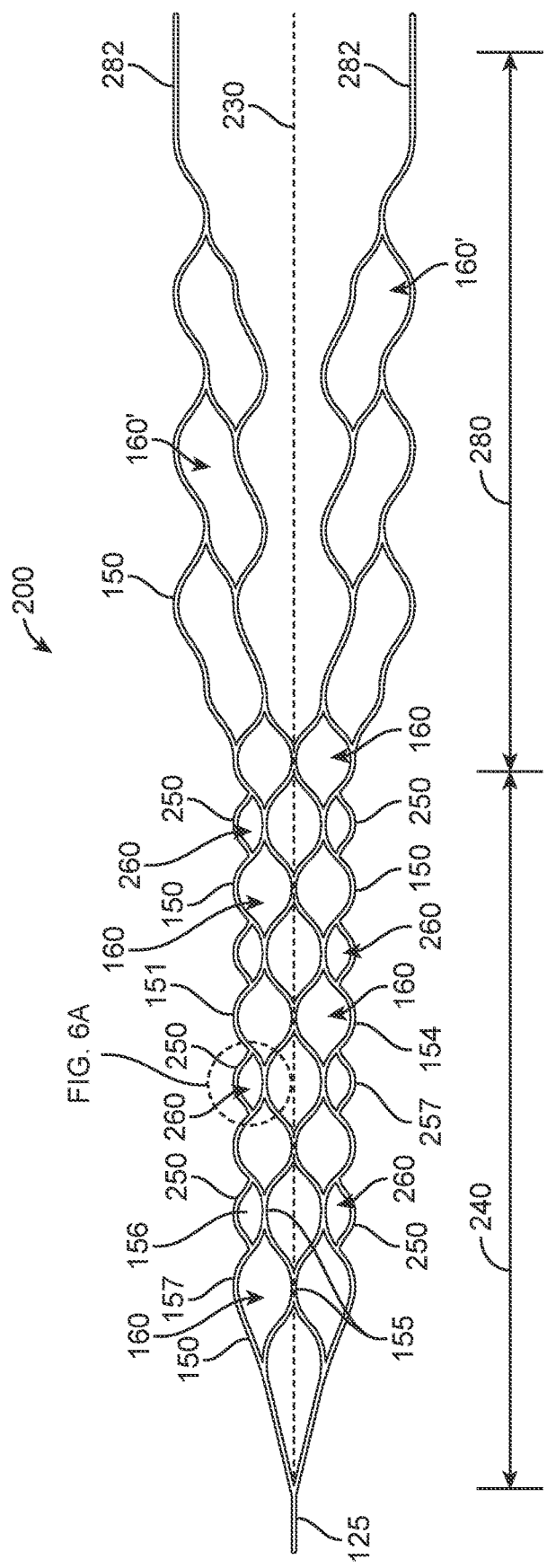
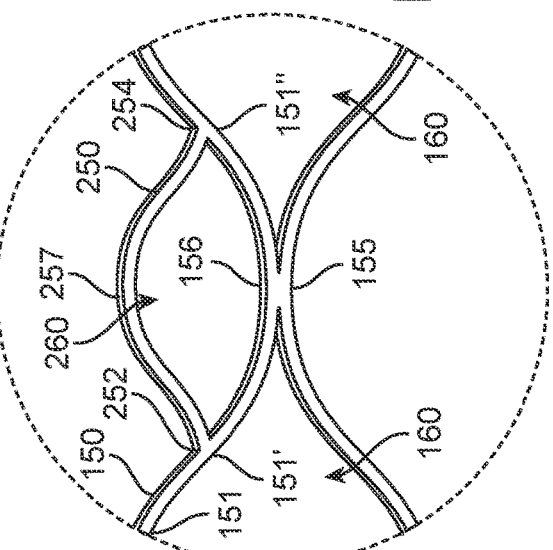
FIG. 6
FIG. 6A

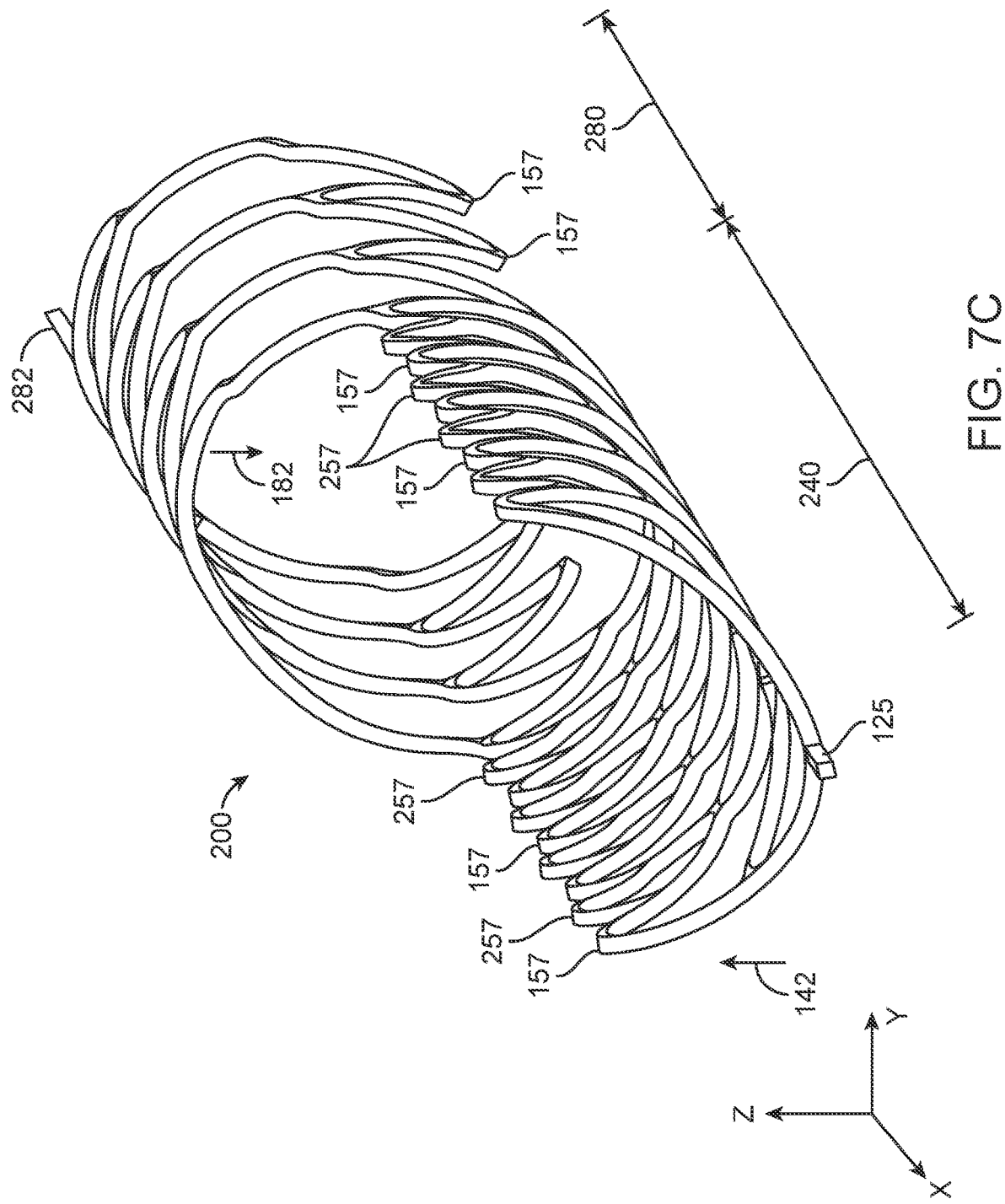

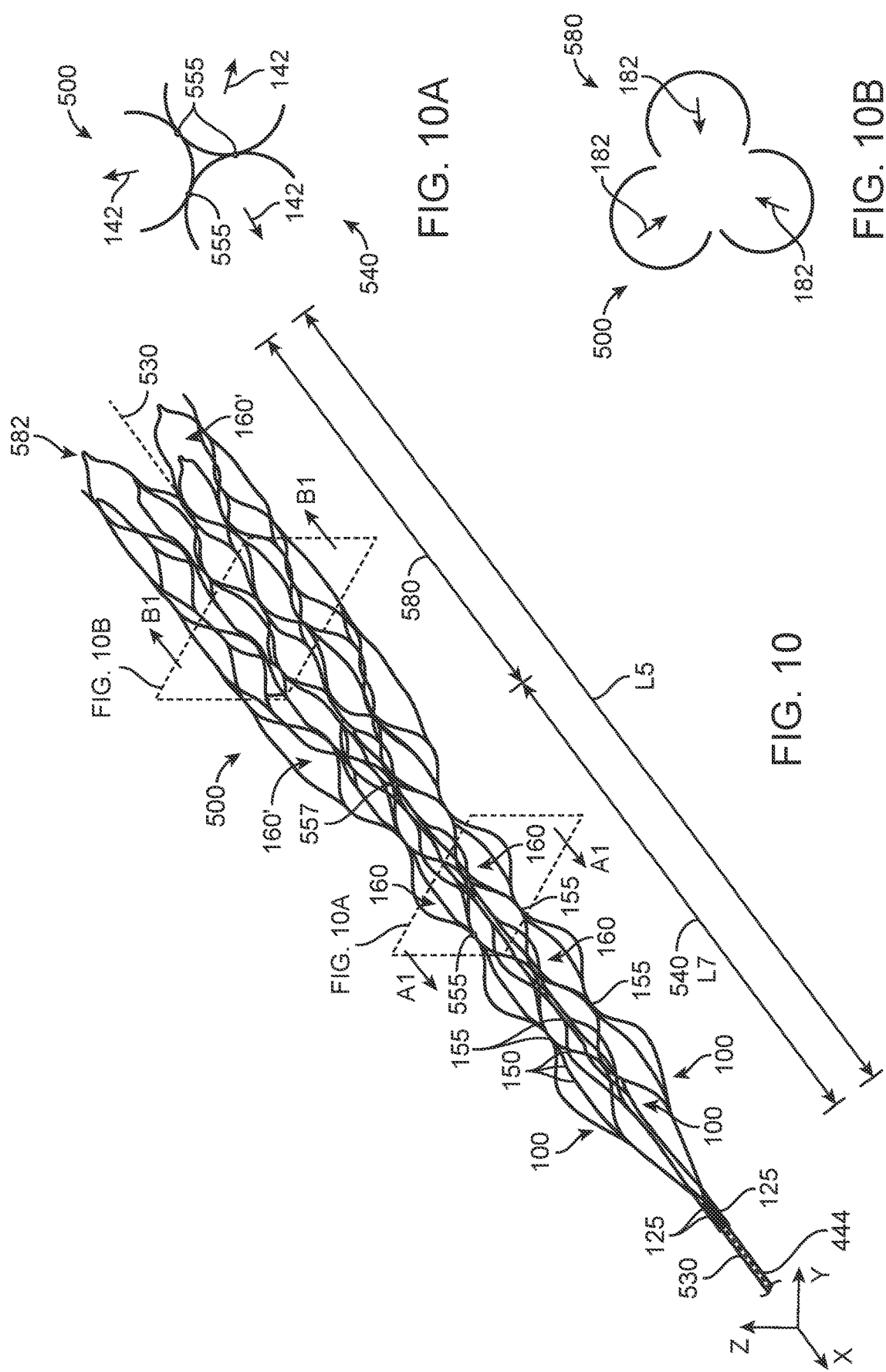

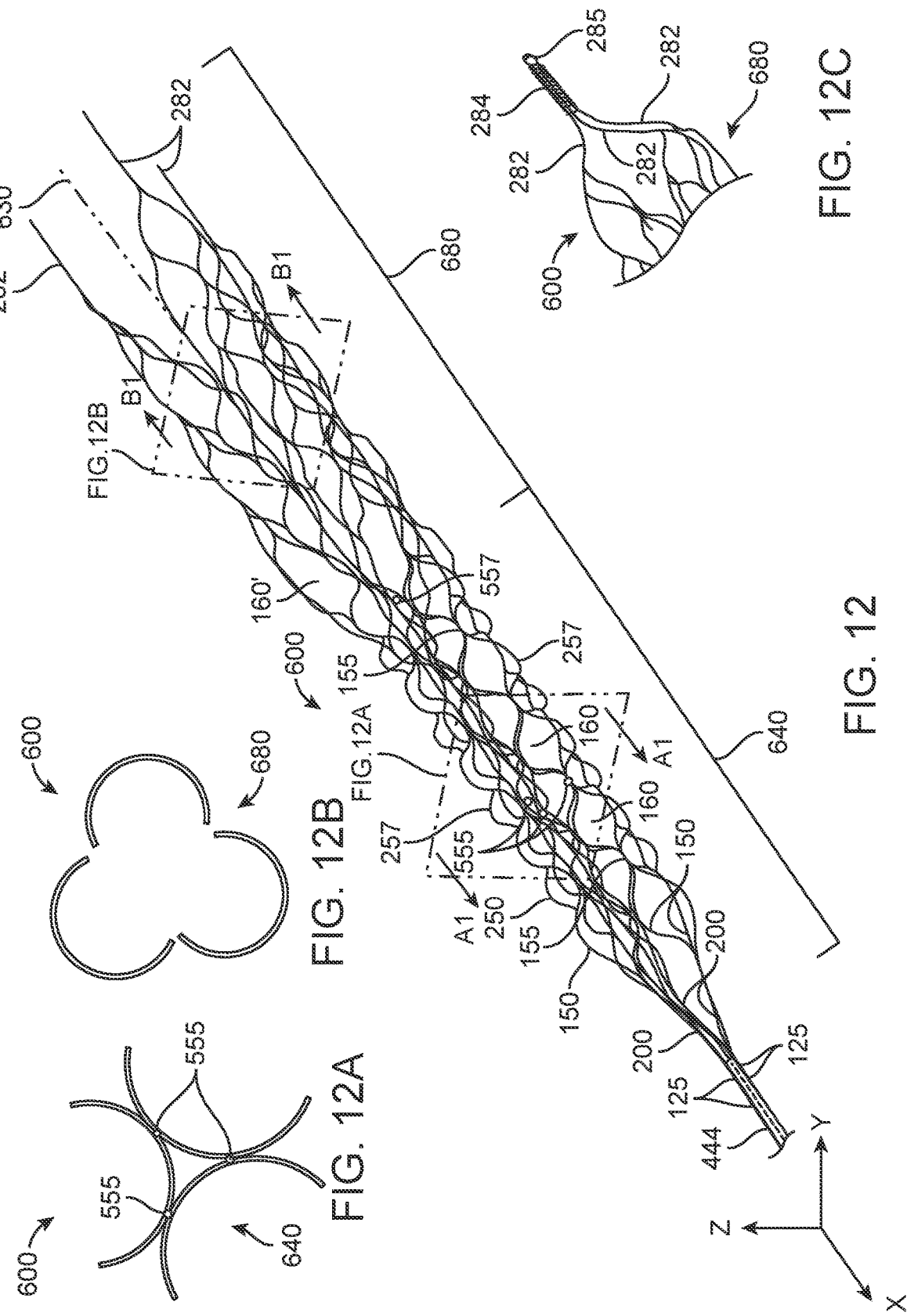

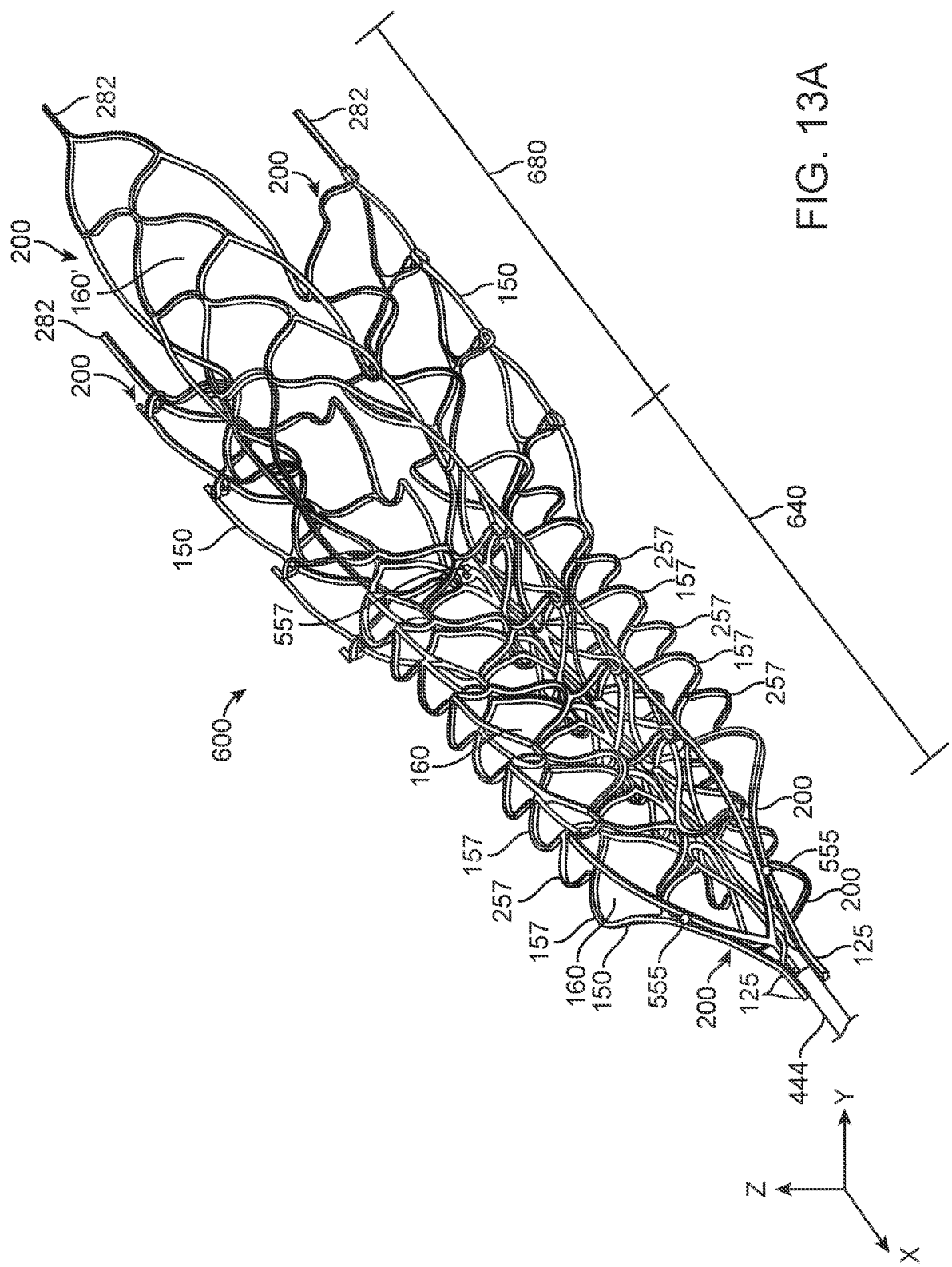

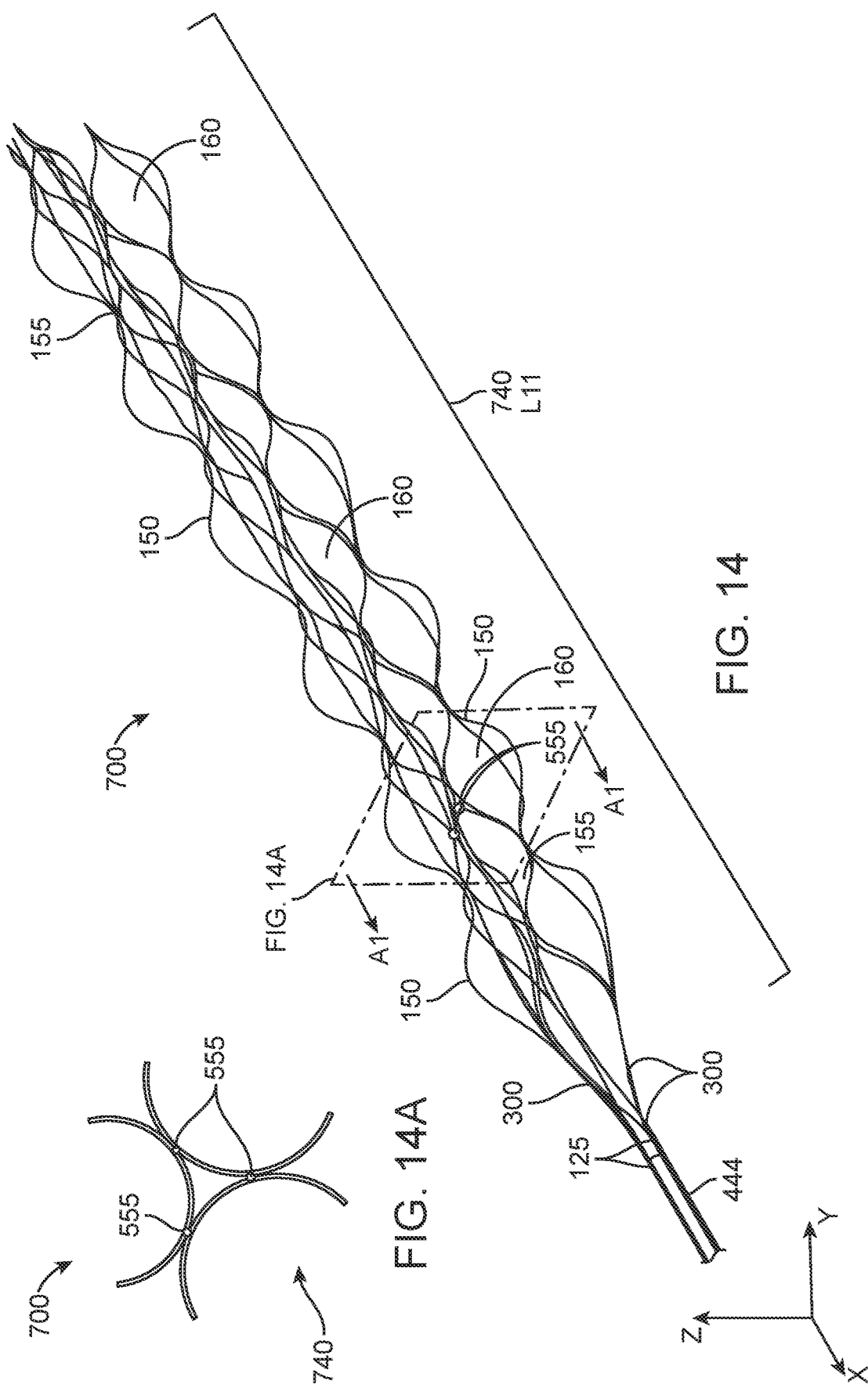

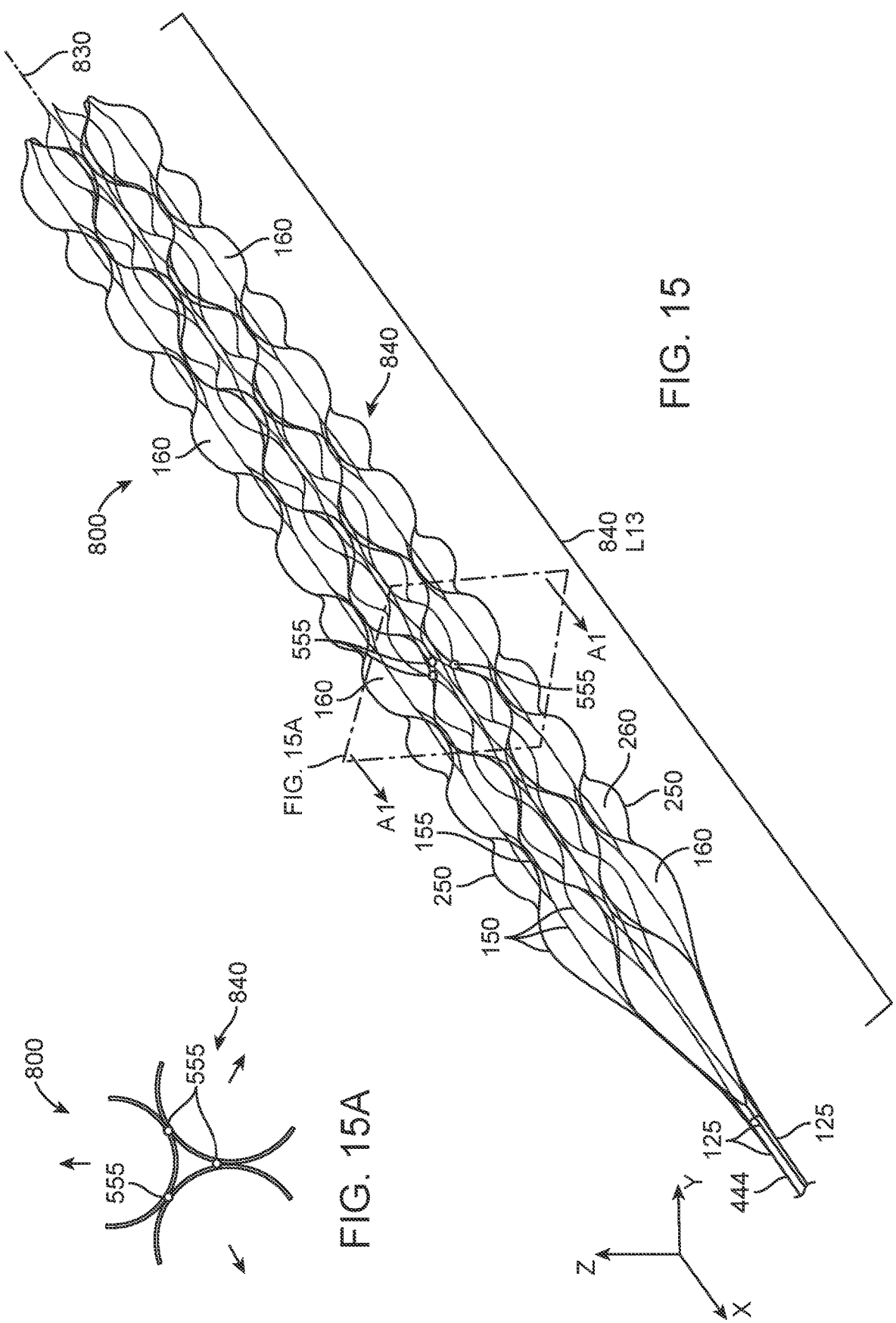

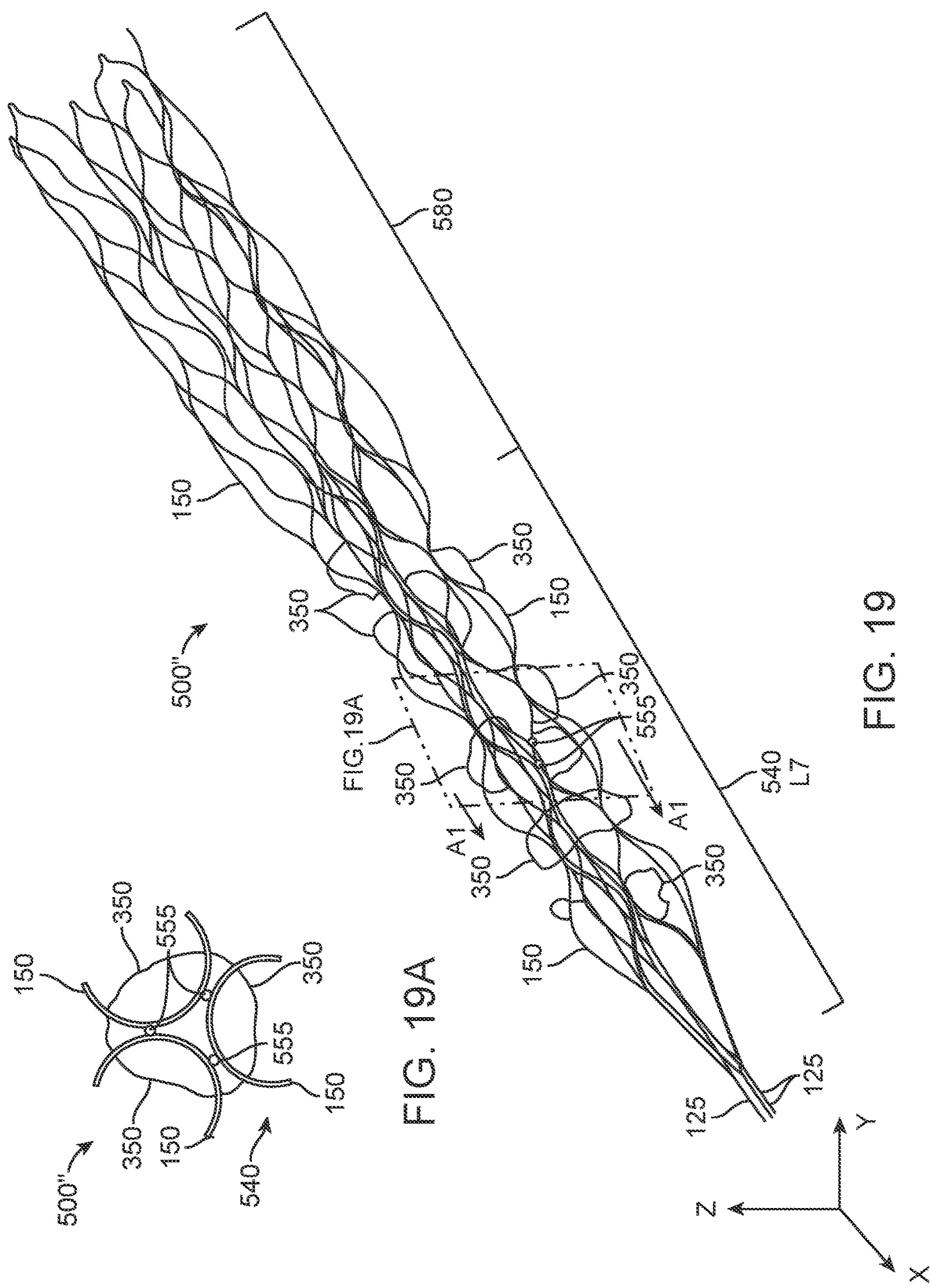

EMBOLECTOMY DEVICE HAVING MULTIPLE SEMI-TUBULAR CLOT ENGAGING STRUCTURES

RELATED APPLICATION DATA

The present is a continuation of U.S. patent application Ser. No. 16/488,121, filed Aug. 22, 2019, which is a National Phase entry under 35 U.S.C § 371 of International Patent Application No. PCT/US2018/019292, having an international filing date of Feb. 22, 2018, which claims the benefit under 35 U.S.C. § 119 to U.S. Provisional Patent Application Ser. No. 62/463,419, filed Feb. 24, 2017, which are all incorporated by reference in their entirety into the present application.

FIELD

The inventions disclosed herein relate generally to medical devices configured for removing embolic obstructions from the vasculature system.

BACKGROUND

Blood thrombus, embolus or clots may occur in a person's vasculature system. Sometimes such clots are harmlessly dissolved in the blood stream. Other times, however, such clots may lodge within a neurovascular blood vessel lumen (i.e., downstream from the carotid arteries), where the clots can partially or completely occlude the flow of blood, referred to as an "ischemic event". If the partially or completely occluded vessel feeds blood to sensitive tissue such as, the brain, lungs or heart, serious tissue damage may result. Such ischemic events may be exacerbated by atherosclerosis, a vascular disease that causes the vessels to become narrowed and/or tortuous. The narrowing and/or increased tortuousness of the blood vessels may, in certain circumstances, lead to the formation of atherosclerotic plaque that can cause further complications.

Known embolectomy devices may be used in a variety of applications to remove blood clots or other foreign bodies from blood vessels. Such devices includes ones cylindrical scaffold embolectomy devices, such those illustrated and described in U.S. Pat. No. 8,529,596 to Grandfield, which is fully incorporated herein by reference. Further, embolectomy devices may include a plurality of scaffolds, such as having an inner cylindrical scaffold concentrically disposed within an outer engaging "stent-basket", or having a plurality of adjacently disposed inner cylindrical scaffolds, as those illustrated and described in U.S. Pat. No. 8,852,205, which is fully incorporated herein by reference.

FIGS. 1A-B illustrate an exemplary prior art embolectomy device 12 that is manufactured and sold by the Neurovascular Division of Stryker Corporation (http://www.stryker.com/en-us/products/NeurovascularIntervention/index.htm). FIG. 1A shows the embolectomy device 12 in a two-dimensional plane view, and FIG. 1B shows the device 12 a three-dimensional expanded tubular configuration. The embolectomy device 12 is composed of shape memory, self-expandable and biocompatible materials, such as Nitinol. The embolectomy device 12 is preferably manufactured by laser cutting a tube or a sheet of shape memory material. The embolectomy device 12 is coupled to an elongate flexible wire 40 that extends proximally from device 12; the wire 40 is configured to push and pull the embolectomy device 12 through sheaths and/or catheters into a target site in a blood vessel.

As shown in FIG. 1A, the embolectomy device 12 includes a includes a proximal end portion 14, a main body portion 16 and a distal end portion 18, the main body portion including a plurality of longitudinal undulating elements 24 (e.g., wires, struts) with adjacent undulating elements being out-of-phase with one another and connected in a manner to form a plurality of diagonally disposed cell structures 26 extending between the respective proximal and distal end portions of the device. The cell structures 26 in the main body portion 16 and distal end portion 18 of the embolectomy device 12 extend continuously and circumferentially around a longitudinal axis 30 of the device 12 (FIGS. 1A-B).

In particular, the cell structures 26 in the proximal end portion 14 extend less than circumferentially around the longitudinal axis 30 of the device 12. The dimensional and material characteristics of the cell structures 26 of the main body portion 16 are selected to produce sufficient radial force (e.g., radial force per unit length of between 0.005 N/mm to 0.050 N/mm, preferable between 0.030 N/mm to 0.050 N/mm) and contact interaction to cause the cell structures 26, and/or the elements 24, to engage with an embolic obstruction residing in the vasculature in a manner that permits partial or full removal of the embolic obstruction from the patient. The out-of-phase configuration of the diagonally disposed cell structures 26 of the device 12 allows distribution of the radial force along the body portion 16, such that the elements 24 engage the obstruction and/or contact the vessel walls in a spiral or non-symmetrical manner, as depicted in FIG. 2, instead of in an annular or symmetrical manner.

As best seen in FIG. 1B, the embolectomy device 12 has an overall length L1 of about 32 millimeters with the main body portion 16 length L2 measuring about 20 millimeters. Usually, the length of the main body portion 16 is generally between about 2.5 to about 3.5 times greater than the length of the proximal end portion 14.

FIG. 2 illustrates the embolectomy device 12 of FIGS. 1A-B disposed in a target site of a tortuous vascular anatomy of a patient capturing an embolic obstruction or clot 75. In an unexpanded or radially compressed configuration (not shown), such as when the embolectomy device 12 is disposed within a delivery catheter 80, the embolectomy device 12 has an unexpanded outer diameter (UOD) between 0.4 to 0.7 millimeters. In a radially expanded configuration (FIGS. 1B-2), the embolectomy device 12 has an expanded outer diameter (EOD) between 2.5 to 5.0 millimeters. The embolectomy device 12 produces sufficient radial force and contact interaction to cause the strut elements 24 and/or cell structures 26 to engage/snare/encapsulate/capture/pinch and/or entrap the embolic obstruction 75 disposed within the blood vessel 70, allowing removal of the embolic obstruction 75 from the patient. The diameter of the main body portion 16 in a fully expanded configuration is about 4.0 millimeters with the cell pattern, elements 24 dimensions and material being selected to produce a radial force of between 0.040 N/mm to 0.050 N/mm when the diameter of the main body portion is reduced to between 1.0 millimeters to 1.5 millimeters. The cell pattern 26, strut dimensions 24 and material(s) are selected to produce a radial force of between 0.010 N/mm to 0.020 N/mm when the diameter of the main body portion 16 is reduced to 3.0 millimeters.

Regardless of the technique used to manufacture the embolectomy device 12, the manner in which the strut elements 24 interconnect determines the device's longitudinal and radial rigidity and flexibility. Radial rigidity is needed to provide the radial force needed to engage the clot or embolic obstruction 75, but radial flexibility is needed to facilitate radial compression of the device 12 for delivery into a target site. Longitudinal rigidity is needed to pull an engaged clot or embolic obstruction 75 from the blood vessel 70, but longitudinal flexibility is needed to facilitate delivery of the device 12 (e.g., through tortuous vasculature). Embolectomy device 12 patterns are typically designed to maintain an optimal balance between longitudinal and radial rigidity and flexibility for the device 12. However, in certain applications, after deployment of the device 12 into the blood vessel 70, and once the embolectomy device 12 is subjected to tension force for retraction or withdrawal, the device 12, particularly, the main body portion 16, tends to stretch creating a smaller profile or outer diameter (OD), similar to the unexpanded outer diameter (UOD) described above (e.g., between 0.4 to 0.7 millimeters).

FIG. 3A illustrates the embolectomy device 12 of FIGS. 1A-B and 2, disposed in a blood vessel 70 distally located from the catheter 80 and having a smaller profile/OD. The stretching of the device 12 and smaller profile/OD may cause the device 12 to be withdrawn past the embolic obstruction 75 without engaging or capturing the obstruction 75, as shown in FIGS. 3A and 3C-G. FIG. 3B-G are cross-sectional views of the blood vessel 70 having a lumen 72 with the embolic obstruction 75 therein. In an embolectomy procedure for removing the embolic obstruction 75 from the blood vessel lumen 72, the delivery catheter 80 is advanced through the lumen 72, until the distal portion of the catheter 80 is disposed in a target site adjacent to the obstruction 75, with the radially compressed embolectomy device 12 disposed within the catheter 80, as shown in FIG. 3C. The embolectomy device 12 is then pushed distally relative to the catheter 80, or the catheter 80 is withdrawn proximally relative to the embolectomy device 12 (or some of each), in order to deploy the device 12 out of the catheter 80 and into the blood vessel lumen 72, allowing the no-longer radially constrained embolectomy device 12 to radially expand within the blood vessel lumen 72 in order to engage, ensnare and capture the obstruction 75.

However, in certain applications (e.g., hard/dense embolic obstruction 75) the radial expansion force 33 of embolectomy device 12 is not sufficient to overcome the hardness and resistive force 36 of the embolic obstruction 75 to allow the struts of device 12 to penetrate into and integrate with the clot 75 minimizing the device 12 outward expansion, as shown in FIG. 3D, or causing the device 12 to take the path of least resistance by extending around the obstruction 75, as shown in FIG. 3E. In other applications, when the radial expansion force 33 exerts and expands the embolectomy device 12, some push 31 and pull 32 forces act and react during the expansion of the device 12, such that not sufficient forces are directed or created to overcome the resistive force 36 of the embolic obstruction 75, as shown in FIG. 3F. Normally, these forces 31/32 in the device 12 allow for a partial or insufficient penetration and/or integration of the struts of device 12 with the obstruction 75, as shown in FIG. 3G. The undesirable minimally expanded profile/OD (FIG. 3D), the elongated profile/OD extending around the obstruction 75 (FIG. 3E) or the less than suitable expansion of the device 12 minimally engaging the obstruction 75 (FIGS. 3F-G) produces none to minimal penetration, integration, engagement and/or ensnaring of the device 12 with the obstruction 75, which tends to pass or leave behind the embolic obstruction 75 without capturing and/or removing the obstruction 75 when the device 12 is withdrawn.

SUMMARY

Embodiments of the disclosed inventions are directed to an embolectomy device biased to expand from a radially constrained configuration to a radially expanded configuration when released from a delivery catheter into a blood vessel, wherein the embolectomy device is formed out of a plurality of elongate clot engaging structures, each clot engaging structure comprising a plurality of interconnected struts forming an open cell pattern. When the embolectomy device is in the radially expanded configuration, each of the clot engaging structures has a semi-tubular arcuate profile, including a convex face and a concave face facing opposite the convex face, extending along a length of the embolectomy device, the clot engaging structures being longitudinally disposed relative to each other such that the respective concave faces are facing radially outward, and the respective convex surfaces are facing radially inward, respectively, relative to a longitudinal axis of the embolectomy device.

In an exemplary embodiment, the embolic device has first, second and third clot engaging structures, wherein one or more struts of the first clot engaging structure are attached to respective one or more struts of the second and third clot engaging structures at one or more attachment locations along a length of the device.

In an exemplary embodiment, respective first and second longitudinal elongate struts of each clot engaging structure are undulating to form successive peaks and intervening valleys along a length of the respective clot engaging structure when the embolectomy device is in the radially expanded configuration. Without limitation, the peaks may be fin-shaped to improve integration with a clot located within the blood vessel. Without limitation, cells defined at least in part by the respective first and second longitudinal elongate struts at the peaks are smaller than cells defined at least in part by the respective first and second longitudinal elongate struts in the valleys.

In an exemplary embodiment, respective first and second longitudinal elongate struts of a first clot engaging structure are symmetrically aligned with the respective first and second longitudinal elongate struts of the other clot engaging structures, wherein the clot engaging structures are attached to one another at one or more attachment locations on the respective first and second elongated struts of each clot engaging structure, wherein the attachment locations are preferably located on od proximate to the longitudinal axis of the embolectomy device. Additionally or alternatively, the clot engaging structures may be attached to a distal end portion of a push wire.

Optionally, a plurality of elongate elements may attached to the struts forming at least one of the clot engaging structures, the elongate elements comprising one or more of filaments, suture material, fibers, threads, wires, or the like.

Further embodiments of the disclosed inventions are directed to an embolectomy device an elongate embolectomy device biased to transition from a radially constrained configuration to a radially expanded configuration, wherein the embolectomy device formed out of a plurality of elongate clot engaging structures, each clot engaging structure comprising a plurality of interconnected struts forming an open cell pattern, and having a proximal active portion and a distal protective portion. In particular, when the embolectomy device is in the radially expanded configuration, the active portion of each clot engaging structure has a semi-tubular arcuate profile, including a convex face and a concave face facing opposite the convex face, the clot engaging structures being longitudinally disposed relative to each other such that the concave faces of the active portions are facing radially outward, and the convex surfaces of the protective portions are facing radially inward, and (ii) the protective portion of each clot engaging structure has a semi-tubular arcuate profile, including a convex face and an concave face facing opposite the convex face, wherein the convex faces of the protective portions are facing radially outward, and the concave surfaces of the protective portions are facing radially inward, respectively, relative to the longitudinal axis of the embolectomy device.

Without limitation, in an exemplary embodiment, a strut of the active portion of a first clot engaging structure is attached to a strut of the active portion of a second clot engaging structure at one or more attachment locations, and the respective protective portions of the first and second clot engaging structures are not attached to one another.

In an exemplary embodiment, plurality of clot engaging structures include first, second, and third clot engaging structures, wherein a strut of the active portion of the first clot engaging structure is attached to a respective strut of the active portions of the second and third clot engaging structures at one or more attachment locations, and wherein the one or more attachment locations are located on or proximate to the longitudinal axis of the embolectomy device.

In various embodiments, struts forming the respective protective portions of the clot engaging structures are coupled at their edges so that the respective protective portions collectively form a trefoil-like barrel shape when the embolectomy device is in the radially expanded configuration.

Optionally, a plurality of elongate elements may be attached to struts of at least one clot engaging structure, wherein the elongate elements may include one or more of filaments, suture material, fibers, threads, wires, and the like.

In an exemplary embodiment, the device further includes a push wire having a distal end portion attached to the respective active portion of each clot engaging structures, wherein the clot engaging structures may also be attached to one another at an attachment location in a transition region between the respective active and protective portions thereof.

In some embodiments, the protective portion of at least one of the clot engaging structures comprises a distal antenna, which may include a marker coil and an atraumatic tip. In one embodiment, the protective portion of each of a plurality of clot engaging structures has a respective distal antenna, wherein the respective distal antennas can be coupled together to form a single marker coil and an atraumatic tip.

In various embodiments, the active portion of each clot engaging structure imparts a greater radial expansion force than is imparted by the respective protective portion of the clot engaging structure when the embolic device transitions from the radially constrained configuration to the radially expanded configuration.

In various embodiments, the active portion of each the clot engaging structure has a substantial same or greater longitudinal length than the respective protective portion of the clot engaging structure when the embolic device is in the radially expanded configuration.

Other and further aspects and features of embodiments of the disclosed inventions will become apparent from the ensuing detailed description in view of the accompanying figures.

BRIEF DESCRIPTION OF THE DRAWINGS

FIGS. 6 and 6A are planar and detailed views of alternative clot engaging device constructed according to another embodiment of the disclosed inventions.

FIGS. 7A-7C are perspective views of the device of FIG. 6.

FIGS. 10, 10A-10B are respective perspective and side views of an exemplary embolectomy device constructed according to embodiments of the disclosed inventions.

FIGS. 12, 12A-12C are respective perspective and side views of an alternative embolectomy device constructed according to embodiments of the disclosed inventions.

FIGS. 13A-13C are perspective views of the embolectomy device of FIGS. 12, 12A-12B.

FIGS. 14 and 14A are perspective and side views of another alternative embolectomy device constructed according to embodiments of the disclosed inventions.

FIGS. 15 and 15A are perspective and side views of still another embolectomy device constructed according to embodiments of the disclosed inventions.

FIGS. 19 and 19A are perspective and side views of the embolectomy device of FIGS. 10, 10A, further including elongated filaments according to still further embodiments of the disclosed inventions.

DETAILED DESCRIPTION OF THE ILLUSTRATED EMBODIMENTS

Figure 1A:
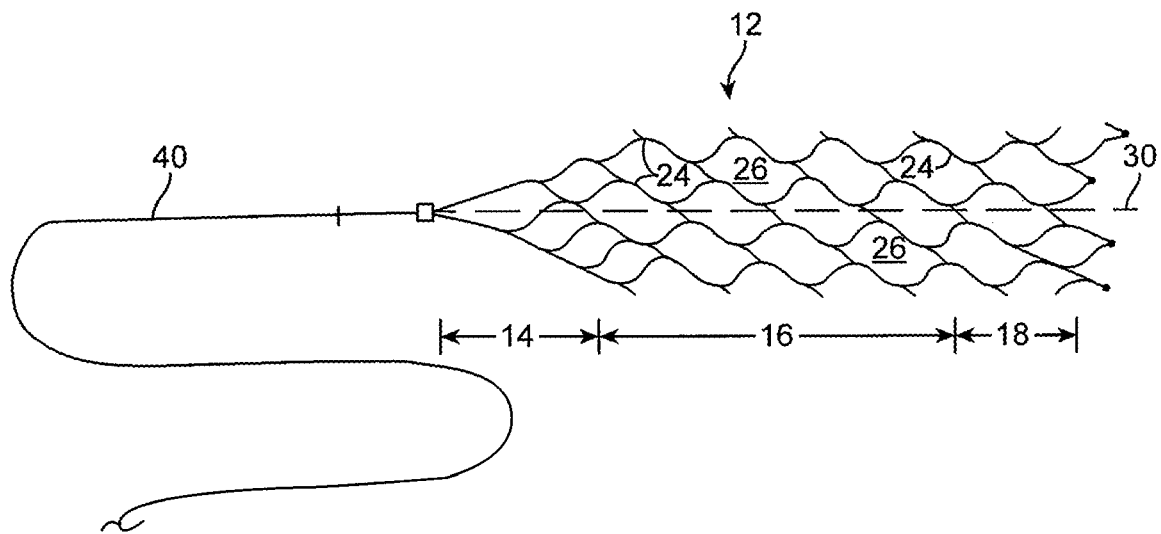
FIGS. 1A-1B are perspective views of a prior art embolectomy device.
Figure 1B:
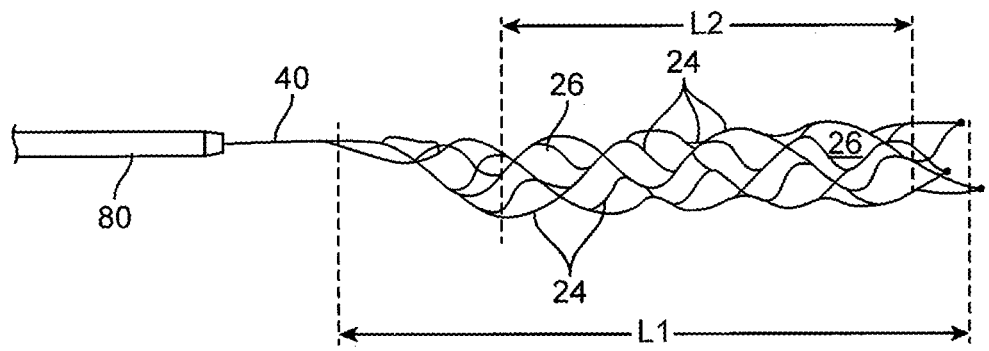

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure. The recitation of numerical ranges by endpoints includes all numbers within that range (e.g., 1 to 5 includes 1, 1.5, 2, 2.75, 3, 3.80, 4, and 5). As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments of the disclosed inventions are described hereinafter with reference to the figures. The figures are not necessarily drawn to scale, the relative scale of select elements may have been exaggerated for clarity, and elements of similar structures or functions are represented by like reference numerals throughout the figures. It should also be understood that the figures are only intended to facilitate the description of the embodiments, and are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated.

Figure 4:
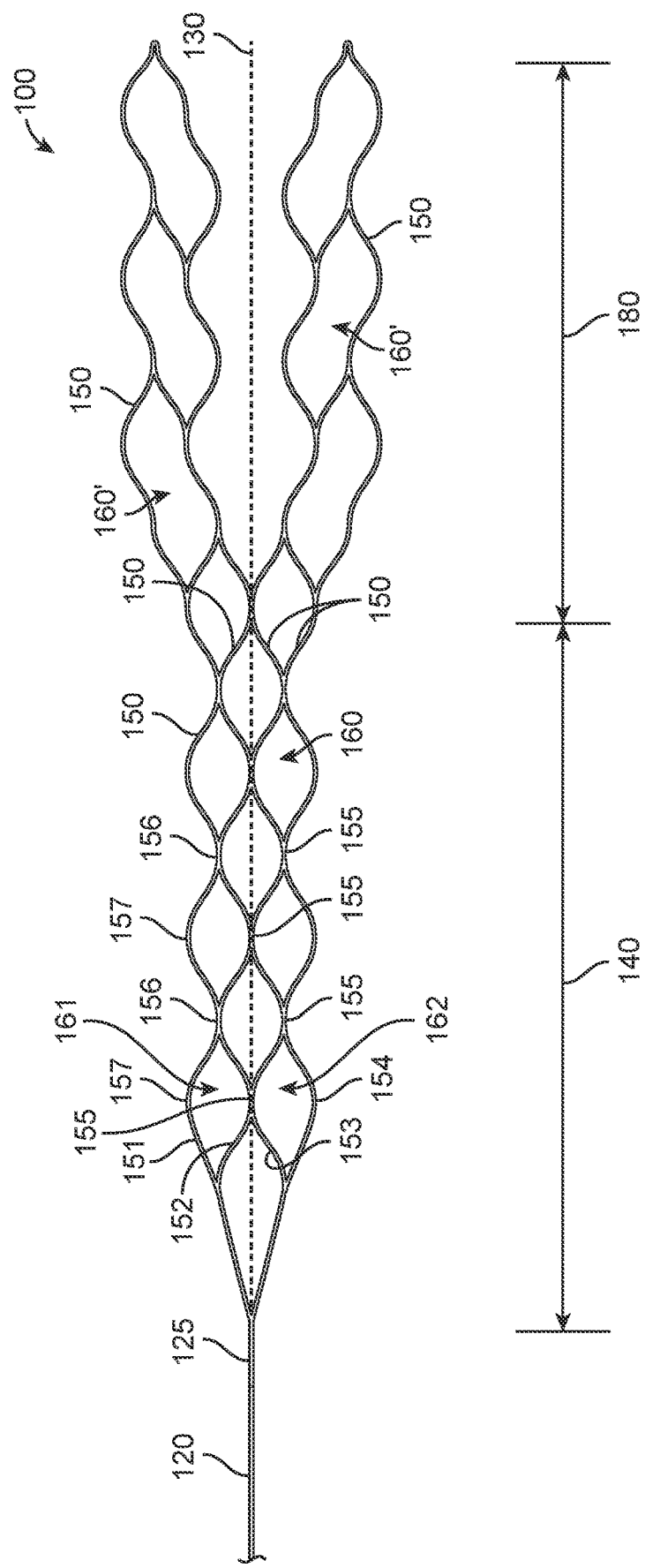
FIG. 4 is a planar and cross-sectional view of an exemplary clot engaging device constructed according to one embodiment of the disclosed inventions.

FIGS. 4 and 5A-C illustrate a clot engaging device 100, constructed in accordance with one embodiment of the disclosed inventions. FIG. 4 depicts the clot engaging device 100 in a two-dimensional plane view, such as if the device were laid flat on a surface. The clot engaging device 100 may be formed of a unitary component (e.g., laser cut of flat sheet or cylindrical, tubular structure, 3D printing, extrusion or the like), or may also include separate components that are welded, bonded or otherwise coupled to one another. By way of non-limiting example of the device when formed of a unitary component, the two-dimensional plane view of FIG. 4 may be used as a cut pattern; such as, placing the pattern over and/or around a tubular structure to manufacture the clot engaging device 100 by laser cutting said pattern into the tubular structure. Further, as used in this specification, the term "coupled" may refer to one or more components that may be directly or indirectly attached, secured, or otherwise, connected. The clot engaging device 100 comprises self-expanding and/or shape memory materials, such as Nitinol, or other suitable materials or combinations thereof (e.g., stainless steel, titanium, platinum, nickel, tantalum, chrome cobalt alloy, or the like). The clot engaging device 100 may include radio-opaque markers or be coated with a layer of radiopaque materials, and comprises a proximal end 125 coupled to an elongate pusher wire 120 that extends proximally from the clot engaging device 100. The proximal end 125 is coupled to the pusher wire 120 by a solder, weld, adhesive, or other suitable attachment methods. The pusher wire 120 is configured to advance and withdraw the clot engaging device 100 through sheaths and/or catheters into a target site in a blood vessel. The clot engaging device 100 comprises a delivery constrained configuration to be translated through sheaths and/or catheters (not shown), and a deployed expanded configuration when the clot engaging device 100 is not radially constrained, such as in FIGS. 5B-C.

As shown in FIG. 4, the clot engaging device 100 includes a proximal portion 140, a distal portion 180, and a central axis 130 extending therebetween, and comprises a plurality of longitudinal undulating elements 150 (e.g., wires, struts, bundle of wires, drawn-filled tubes, or the like). It should be appreciated that a cross-section of elements 150 may be include a continuous configuration or may vary along its length. For example, a cross-section of an element 150 can be circular in a first portion and can be oval in a second portion (not shown). Each undulating element 150 comprises a sinusoid configuration defining respective maximum/peak regions 157 and minimum/valley regions 156, so that the adjacently disposed undulating elements 150 form a plurality of adjacently disposed cells 160.

For example, a first undulating element 151 is coupled to a second undulating element 152 at respective connection points 155 between a respective valley region 156 of element 151 and peak region 157 of element 152, thereby forming cells 160. Further, a fourth undulating element 154 is coupled to a third undulating element 153 at respective connection points 155 between a respective peak region 157 of element 154 and valley region 156 of element 153, thereby forming further cells 160. The second undulating element 152 is further coupled to the third undulating element 153 at respective connection points 155 forming cells 160. The first undulating element 151 and the fourth undulating element 154 are the outwardly disposed undulating elements, and the second undulating element 152 and the third undulating element 153 are inwardly disposed undulating elements. The connection points 155 between the adjacently disposed undulating elements 150 are symmetrically disposed with respect to the central axis 130 of the device 100, such that the cells 160 are adjacently disposed with respect to each other.

By way of another non-limiting example, a first cell 161 is adjacently disposed to second cell 162 at the proximal portion 140 of the device 100, as shown in FIG. 4. The cell structures 160 of the proximal portion 140 of the clot engaging device 100 comprise a "lemon-like" configuration, while the cell structures 160' of the distal portion 180 of the clot engaging device 100 comprise a "peanut-like" configuration. The cell structures 160' of the distal portion 180 are larger than the cell structures 160 of the proximal portion 140 of the clot engaging device 100. It should be appreciated that the shape and configuration of the cells 160 and 160' depicted in FIG. 4 are exemplary and not intended to limit the embodiment of the clot engaging device 100. The cells 160 may comprise a "diamond-like" configuration, where the element 150 form angular shaped peaks 157 (not shown). It should be further appreciated that the clot engaging device 100, including the undulating elements 150 may have an alternative shapes, and other suitable configurations. Other variations of the clot engaging devices, such as the configuration of the undulating elements are contemplated, such as the exemplary configurations depicted in FIGS. 8 and 9.

Figure 5A:
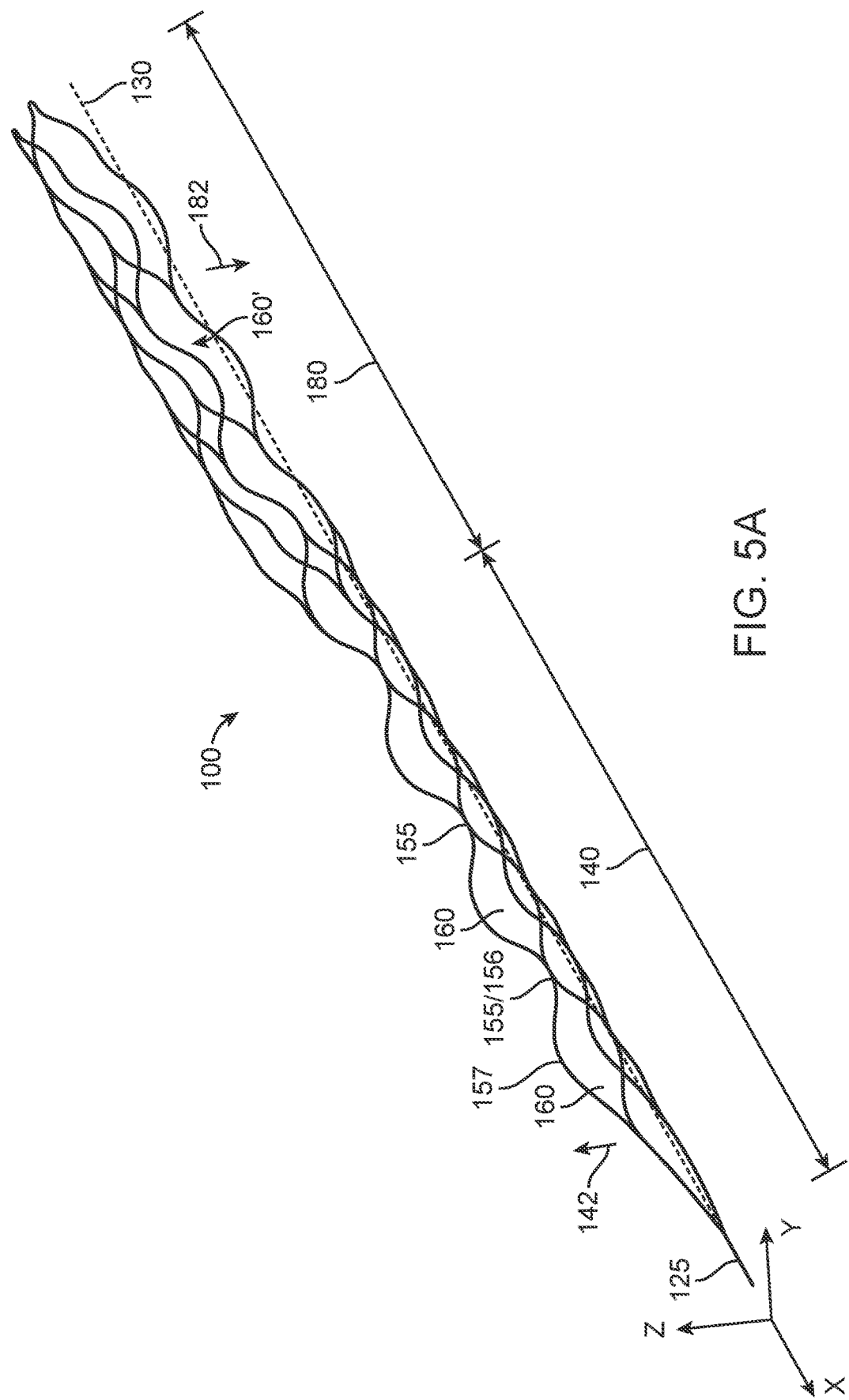
FIGS. 5A-C are perspective views of the device of FIG. 4.
Figure 5B:
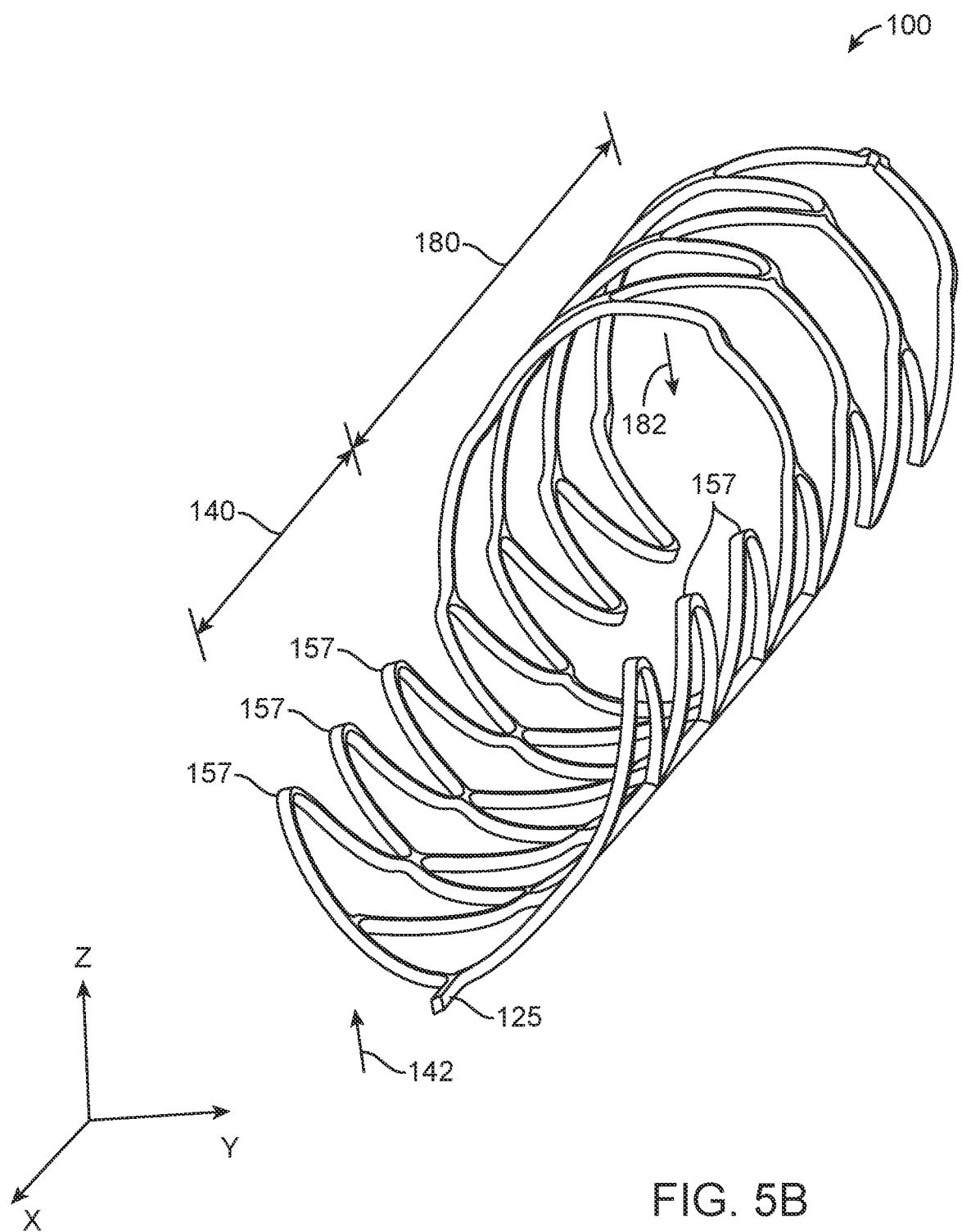
Figure 5C:
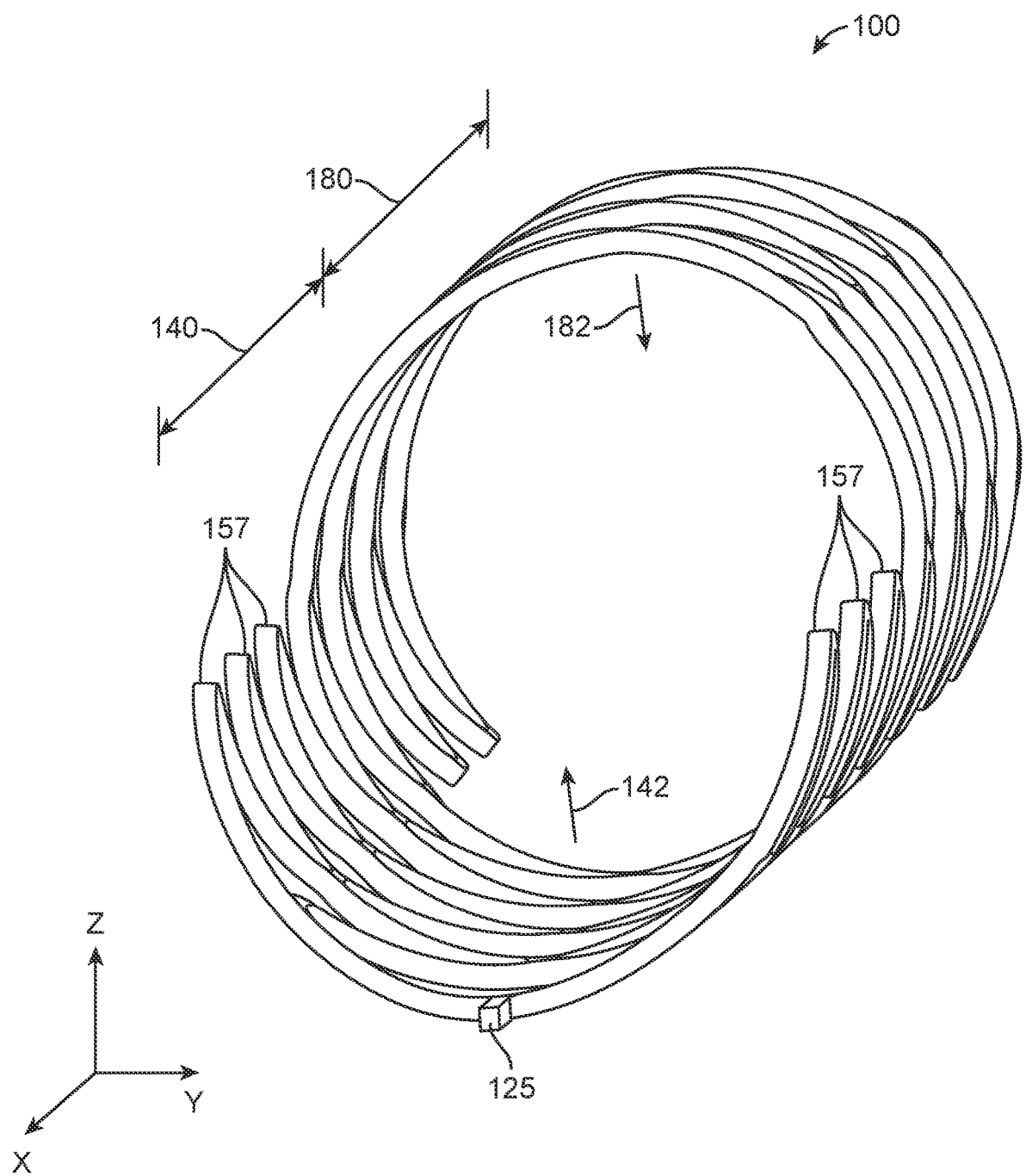

FIGS. 5A-C depict the clot engaging device 100 of FIG. 4 in perspective three-dimensional views of the device expanded configuration. FIG. 5A depicts the clot engaging device 100 in a perspective side view of the expanded configuration, such as having the proximal end 125 and central axis 130 of the device 100 disposed parallel to the x-axis in the 3D Cartesian coordinate system. FIGS. 5A-C depict the clot engaging device 100 in further perspective views of the expanded configuration, such as having the proximal end 125 of the device 100 translated along the y-axis in the 3D Cartesian coordinate system. In the expanded configuration of the clot engaging device 100, the proximal portion 140 and distal portion 180 of the device 100 include respective arcuate configurations, as shown in FIGS. 5A-C.

The arcuate configuration of the proximal portion 140 (e.g., concave surface facing outwardly or up 142) of the clot engaging device 100 is configured to face an opposite direction as the arcuate configuration of the distal portion 180 (e.g., concave surface facing inwardly or down 182) of the device, as shown in FIGS. 5A-C. The at least two distinct portions, proximal 140 and distal 180 of the clot engaging device 100, having opposite facing arcuate configurations and/or semicircular profiles define, outline or contour a "fin-like" configuration of the maximum/peak regions 157 of elements 150 (FIGS. 5A-C). The "fin-like" configuration of the maximum/peak regions 157 of elements 150 are configured to engage, snare, integrate, capture and/or entrap embolic obstructions 75 disposed within a blood vessel, as it will be described in further detail below.

FIGS. 6, 6A and 7A-C illustrate an alternate embodiment of a clot engaging device 200, constructed in accordance with embodiments of the disclosed inventions. For ease in illustration, the features, functions, and configurations of the clot engaging device 200 of FIGS. 6, 6A and 7A-C that are the same as in the device 100 shown FIGS. 4 and 5A-C are given the same reference numerals. FIG. 6 depicts the clot engaging device 200 in a two-dimensional plane view, such as if the device were laid flat on a surface. Similar to device 100, the clot engaging device 200 may be formed of a unitary component or may include separate components that are welded, bonded or otherwise coupled to one another, as previously disclosed. By way of a non-limiting example of the device when formed of a unitary component, the two-dimensional plane view of FIG. 6 may be used as a cut pattern; such as, placing the pattern over and/or around a tubular structure to manufacture the clot engaging device 200 by laser cutting said pattern into the tubular structure.

The clot engaging device 200 comprises self-expanding and/or shape memory materials, such as Nitinol, or other suitable materials or combinations thereof, and further includes a delivery constrained configuration and a deployed expanded configuration. The clot engaging device 200 comprises a proximal portion 240, a distal portion 280, and some of the same features as the above-described device 100, such as a proximal end 125 and central axis 130. Also similar to device 100, the clot engaging device 200 comprises a plurality of longitudinal undulating elements 150 (e.g., stainless steel, titanium, platinum, nickel, chrome cobalt alloy, or the like), each undulating element 150 having a sinusoid configuration defining respective maximum/peak regions 157 and minimum/valley regions 156, where the adjacently disposed undulating elements 150 form a plurality of adjacently disposed cells 160. Connection points 155 between the adjacently disposed undulating elements 150 are symmetrically disposed with respect to the central axis 130 of the device 200, such that the cells 160 are adjacently disposed with respect to each other.

One difference from the device 100 is that the clot engaging device 200 further includes a plurality of elongated elements 250 (e.g., wires, struts, bundle of wires, drawn-filled tubes, or the like) having respective first ends 252 and second ends 254 coupled to the outwardly disposed undulating elements 150 (i.e., first 151 and fourth 154 elements) in the proximal portion 240 of the device 200. For example, the first end 252 of one elongated element 250 is coupled to a first portion 151' of the first undulating element 151 and the second end 254 of one elongated element 250 is coupled to a second portion 151" of the first undulating element 151, the first and second portions 151' and 151" are disposed between a valley region 156, as shown in detailed FIG. 6A. A first plurality of elongated elements 250 are coupled to the undulating element 151 and a second plurality of elongated elements 250 are coupled to the element 154, each elongated elements 250 having a maximum/peak region 257 and forming respective cells 260. The elongated elements 250 are configured to be coupled to the outwardly disposed undulating elements 150 (i.e., first 151 and fourth 154 elements) to provide further elements to snare and/or engage with an embolic obstruction residing in the vasculature of a patient. The cell 260 comprise "lemon-like" configuration smaller than the cells 160 of the proximal portion 140 of the clot engaging device 200. The cells 260 formed between the first undulating element 151 and the plurality of elongated members 250 are symmetrically disposed with respect to the central axis 130, so as to be symmetrically disposed with respect to the cells 260 formed between the fourth undulating element 154 and the plurality of elongated members 250.

It should be appreciated that the shape and configuration of the cells 260 in FIGS. 6 and 6A are exemplary and not intended to limit the embodiment of the clot engaging device 200. For example, the cells 260 may comprise a "diamond-like" configuration, where the element 250 form angular shaped peaks 257 (not shown). In another alternative example, the cell 160 may comprise a "diamond-like" configuration (not shown), having the elements forming angular shaped peaks 157, while the cells 260 comprise the "lemon-like" configuration.

The distal portion 280 of the clot engaging device 200 is similar to the distal portion 180 of device 100, having undulating elements 150 forming cells 160'. The distal portion 280 of device 200 further includes one or more elongated distal ends or antennas 282 extending distally from the undulating elements 150 of the distal portion 280, as shown in FIG. 6. The elongated distal ends or antennas 282 are coupled to each in the expanded configuration of the clot engaging device 200, as shown in FIGS. 7A-C.

Figure 7A:
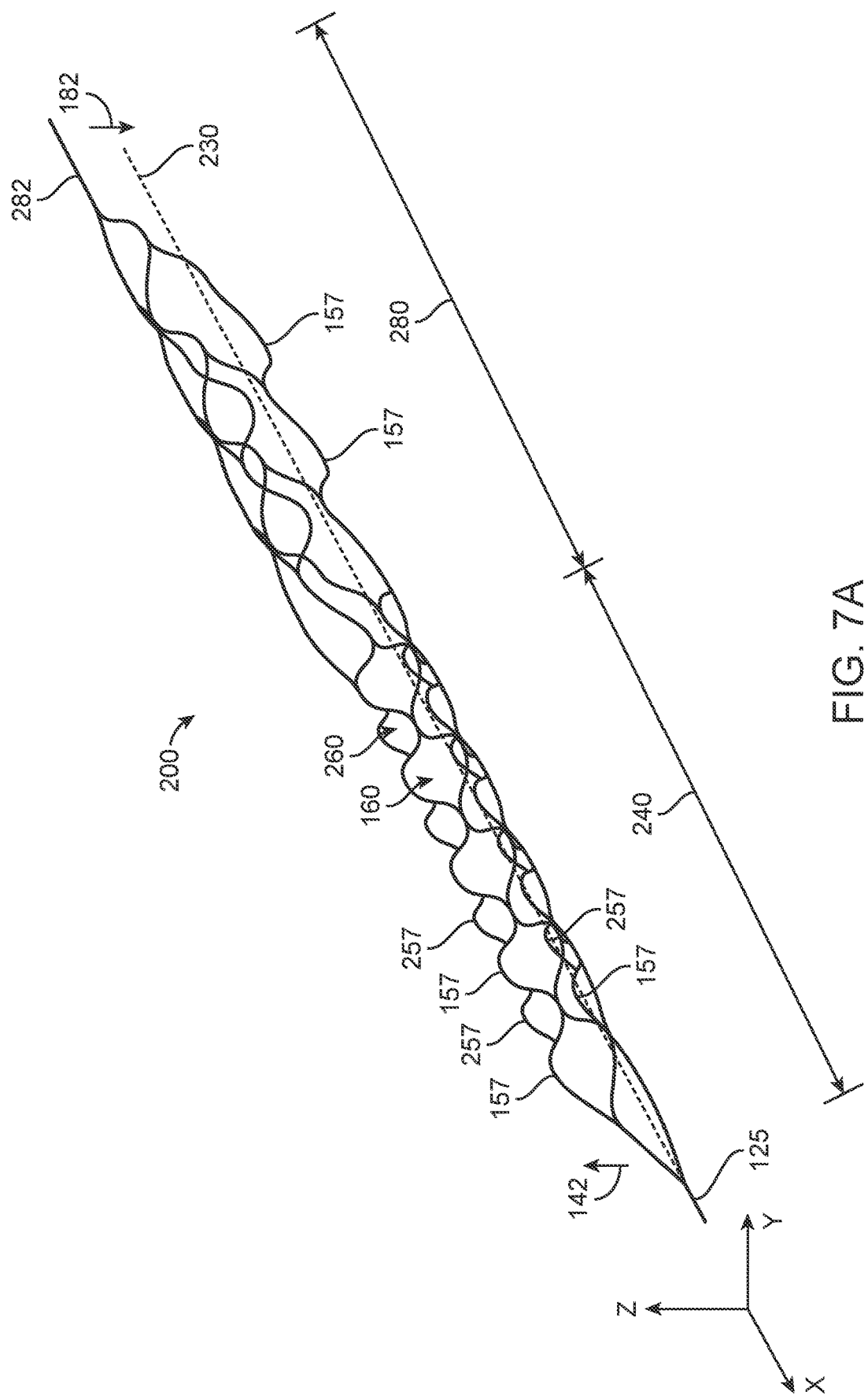
Figure 7B:
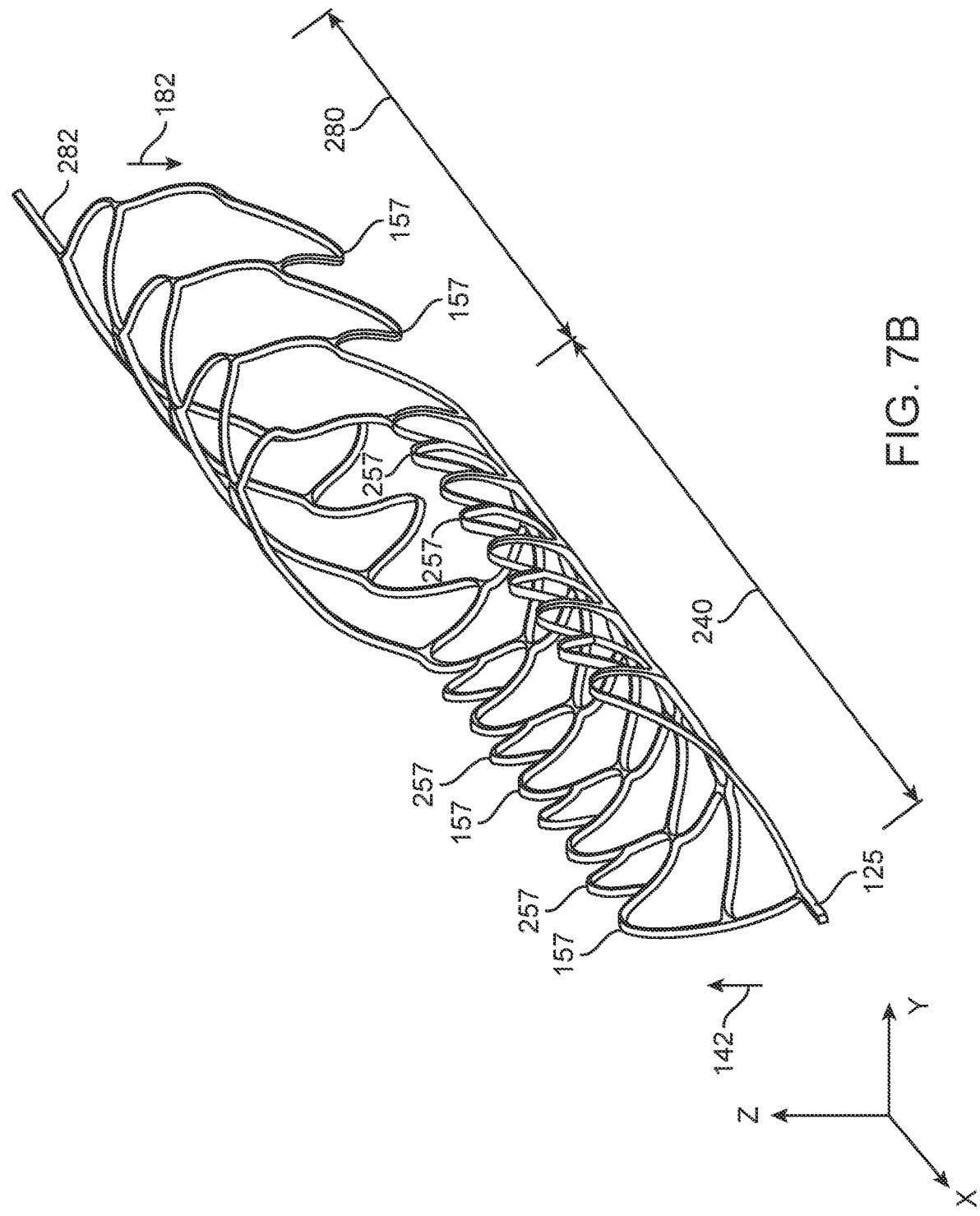

FIGS. 7A-C depict the clot engaging device 200 of FIG. 6 in perspective three-dimensional views of the device expanded configuration. FIG. 7A depicts the clot engaging device 200 in a perspective side view of the expanded configuration, such as having the proximal end 125 of the device 200 disposed parallel to the x-axis in the 3D Cartesian coordinate system. FIGS. 7A-C depict the clot engaging device 200 in further perspective views of the expanded configuration, such as having the proximal end 125 of the device 200 translated along the y-axis in the 3D Cartesian coordinate system. In the expanded configuration, the proximal portion 240 and distal portion 280 of the device 200 include respective arcuate configurations, as shown in FIGS. 7A-C. The semi-tubular arcuate configuration of the proximal portion 240 (e.g., concave surface facing outwardly or up 142) is configured to face an opposite direction as the arcuate configuration of the distal portion 280 (e.g., concave surface facing inwardly or down 182) of the device, as shown in FIGS. 7A-C. The at least two distinct portions, proximal 240 and distal 280 of the device 200, having opposite facing arcuate configurations and/or semicircular profiles define, outline or contour a "fin-like" configuration. The proximal portion 240 of the device 200 defines, outline or contours the "fin-like" configuration by a combination of the maximum/peak regions 157 of elements 150 and the maximum/peak regions 257 of the elements 250, as better appreciated in FIGS. 7B-C. The proximal portion 240 of the device 200 includes more maximum/peak regions and/or denser "fin-like" configuration than the proximal portion 140 of the device 100. The distal portion 280 of the device defines, outline or contours the "fin-like" configuration by the maximum/peak regions 157 of elements 150, similar to the distal portion 180 of device 100. The "fin-like" configuration of the maximum/peak regions 157 and 257 of device 200 are configured to engage, snare, integrate, capture and/or entrap embolic obstructions disposed within a blood vessel, as it will be described in further detailed below.

Figure 8:
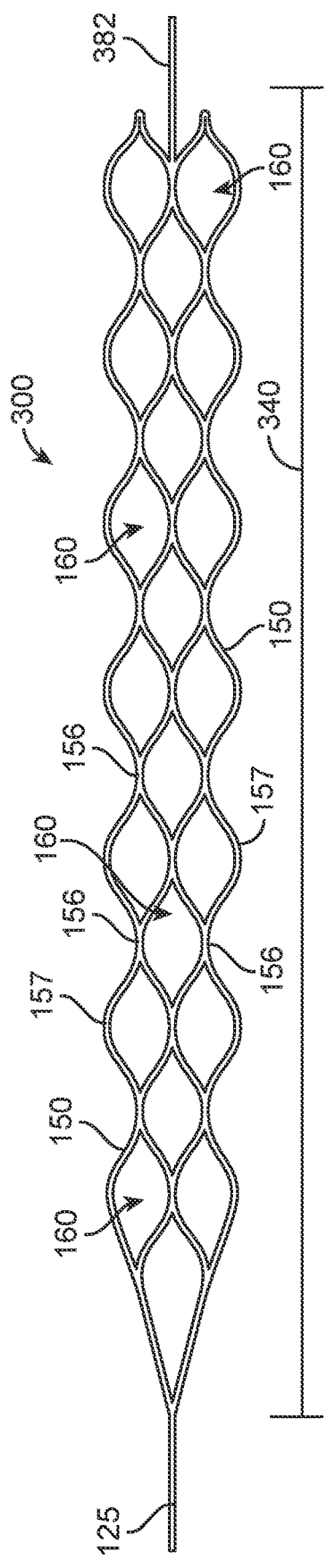
FIG. 8 is a planar view of a further alternative clot engaging device constructed according to yet another embodiment of the disclosed inventions.
Figure 9:
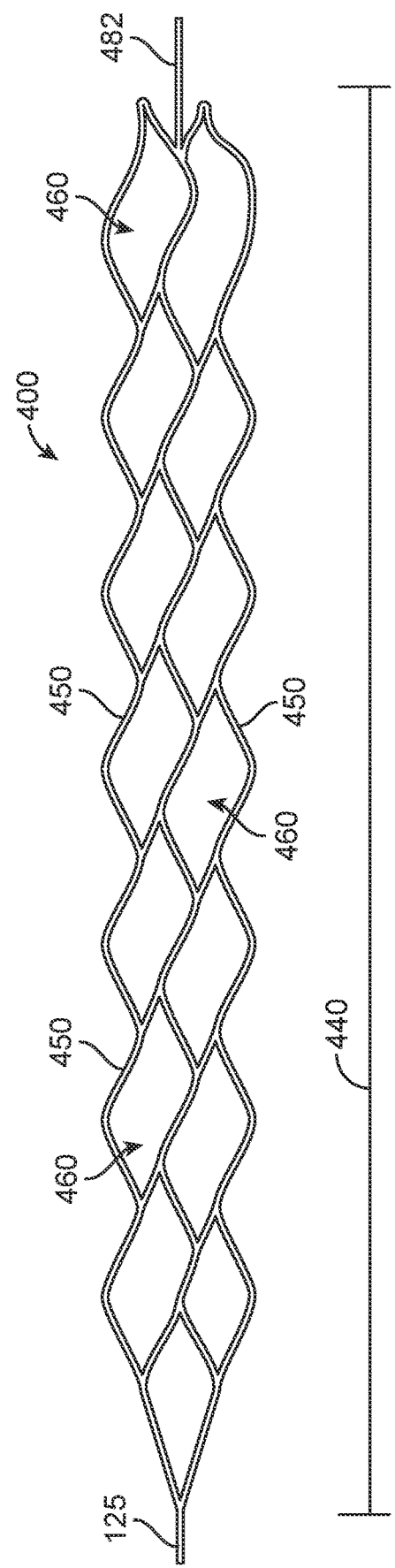
FIG. 9 is a planar view of yet another clot engaging device constructed according to still another embodiment of the disclosed inventions.

FIGS. 8 and 9 illustrate further embodiments of clot engaging devices 300 and 400 constructed in accordance with various embodiments of the disclosed inventions. For ease in illustration, the features, functions, and configurations of device 300 of FIG. 8 and device 400 of FIG. 9 that are similar or same as in the previously disclosed devices 100 and/or 200 are given the same reference numerals. FIGS. 8 and 9 depict the respective clot engaging devices 300 and 400 in a two-dimensional plane view, such as if the devices were laid flat on a surface. Similar to the device 100, the clot engaging devices 300 and 400 may be formed of a unitary component or may include separate components, comprises self-expanding and/or shape memory materials, or other suitable materials or combinations thereof, as previously disclosed. The clot engaging devices 300 and 400 include delivery constrained configurations and a deployed expanded configuration.

FIG. 8 illustrates the clot engaging device 300 having a proximal end 125, a body portion 340, and a distal end 382. The proximal 125 and distal 382 ends include a longitudinal wire, strut, antenna or the like. Similar to the proximal portion 140 of de device 100 of FIG. 4, the body portion 340 of the device 300 of FIG. 8 comprises a plurality of undulating elements 150 (e.g., wires, struts, bundle of wires, drawn-filled tubes, or the like), each undulating element 150 having a sinusoid configuration defining respective maximum/peak regions 157 and minimum/valley regions 156, so that the adjacently disposed undulating elements 150 form a plurality of adjacently disposed cells 160. Each cell 160 of the device 300 comprises a "lemon-like" configuration and is symmetrically disposed with a respective adjacent cell. The deployed expanded configuration of the clot engaging device 300 forms an arcuate configuration, as shown for the proximal portion 140 of the device 100 in FIGS. 5A-C.

FIG. 9 illustrates the clot engaging device 400 having a proximal end 125, a body portion 440, and a distal end 482. The proximal 125 and distal 482 ends include a longitudinal wire, strut, antenna or the like. FIG. 9 comprises a plurality of undulating elements 450 (e.g., wires, struts, bundle of wires, drawn-filled tubes, or the like) being out-of-phase with one another and connected in a manner to form a plurality of diagonally disposed cell structures 460 extending throughout the body portion 440 of the device 400. The out-of-phase of the diagonally disposed cell structures 460 of the device 400 allows distribution of the radial force along the body portion 440, such that the elements 450 engage the obstruction and/or contact the vessel walls in a spiral or non-symmetrical manner.

FIGS. 10, 10A-B, and 11A-C illustrate an embolectomy device 500, constructed in accordance with embodiments of the disclosed inventions. The embolectomy device 500 comprises a plurality of clot engaging devices 100 of FIGS. 4 and 5A-C. FIG. 10 depicts the embolectomy device 500 having three clot engaging devices 100 coupled to each other in a "back-to-back" expanded configuration, as better appreciated in FIGS. 10A-B, 11A-C. The embolectomy device 500 includes a proximal portion 540, a distal portion 580, and a central axis 530 extending therebetween. Each of the clot engaging devices 100 forming the embolectomy device 500 comprises a plurality of longitudinal undulating elements 150 (e.g., wires, struts, bundle of wires, drawn-filled tubes, or the like) having respective sinusoid configurations so that adjacently disposed undulating elements 150 form a plurality of adjacently disposed cells 160. The undulating elements 150, connection points 155 between the elements 150, and cells 160 of the respective proximal portions 140 of the devices 100 are symmetrically disposed with a respect to their respective central axis 130, as previously disclosed in FIG. 4. The embolectomy device 500 has an overall length L5 of approximately 30 millimeters with the proximal portion 540 length L7 measuring approximately between 10 to 20 millimeters. In the embodiment of FIG. 10, the proximal portion 540 and the distal portion 580 have approximately the same length. In some embodiments, the length of the proximal portion 540 is generally between 0.5 to 3.5 times greater than the length of the distal portion 580. In an unexpanded or radially compressed configuration (not shown), such as when the embolectomy device 500 is disposed within a delivery catheter, the embolectomy device 500 has an unexpanded outer diameter (UOD) between 0.4 to 0.7 millimeters. In a radially expanded configuration (FIGS. 10, 11A-C), the proximal portion 540 of the embolectomy device 500 comprises an expanded outer diameter (EOD) between 1.5 to 5.0 millimeters, and the distal portion 580 of the device 500 comprises an expanded outer diameter (EOD) between 1.5 to 6.0 millimeters.

The embolectomy device 500 is shown in a perspective side view of the expanded configuration in FIG. 10, such as having respective proximal ends 125 of each of the clot engaging devices 100, and the central axis 530 of the device 500 disposed parallel to the x-axis in the 3D Cartesian coordinate system. Each of the proximal portions 140 of the clot engaging devices 100 are coupled, attached, or otherwise secured to each other forming embolectomy device 500. Due to the symmetry of the undulating elements 150, connection points 155 between the elements 150, and cells 160 of the respective proximal portions 140 of the clot engaging devices 100, some points, sections or areas of the undulating elements 150 of one of the clot engaging devices 100 are configured to contact respective points, sections or areas of the undulating elements 150 of the other two adjacently disposed clot engaging devices 100 in a "back-to-back" configuration. As better appreciated in the side (profile) view of FIG. 10A, seen from the cross-sectional plane of the proximal portion 540 of the device 500 at FIG. 10 viewed towards the proximal ends 125, as indicated by arrows "A1", the respective points, sections or areas of undulating elements 150 are coupled, attached or secured by connectors 555 to respective adjacent undulating elements 150. The connectors 555 comprise direct or indirect coupling, attachment or securement, such as, by adhesive, thermal bonding, welding, interlocking geometries, mechanical fastening, or the like or combinations thereof. The arcuate expanded configurations of the respective clot engaging devices 100 are configured to face outwardly (e.g., concave surface facing outwardly 142) in the proximal portion 540 of the device 500, as shown in FIGS. 10A and 11A-C. When the device 500 expands from the constricted configuration, the respective arcuate configuration of the clot engaging devices 100 produce sufficient outwardly and/or radial force (e.g., radial force per unit length of between 0.005 N/mm to 0.050 N/mm, preferable between 0.030 N/mm to 0.050 N/mm) to snare, engage and/or otherwise capture an obstruction in the vasculature, as it will be described in further detail below.

Figure 17:
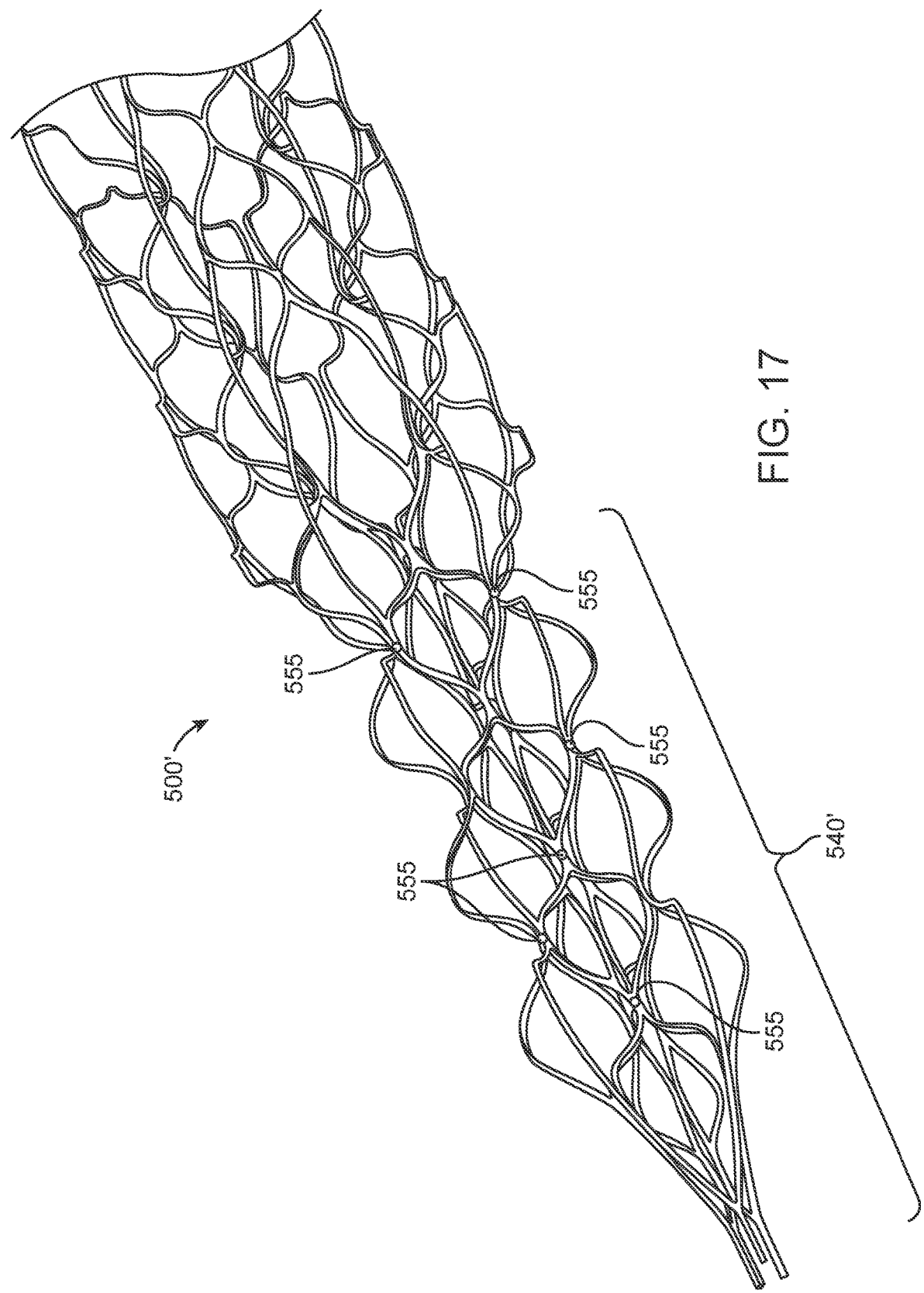
FIG. 17 is a perspective view of an embolectomy device having connectors, constructed according to further embodiments of the disclosed inventions.

It should be appreciated that the proximal portion 540 of the device 500 may include connectors 555 in all, substantially all, most (FIGS. 10-11C) or selectively in some (e.g. FIG. 17) of the respective points, sections or areas where the undulating elements 150 contact each other. For example, in some embodiments of a device 500', such as in FIG. 17, the connectors 555 are alternatively or selectively disposed between some of the respective proximal portions 140 of the clot engaging devices 100 forming the proximal portion 540'. The device 500' of FIG. 17 is substantially similar to the device 500 of FIGS. 10-11C, with the difference that the proximal portion 540' of the device 500' includes selectively disposed connectors 555. The quantity of connectors 555 that the proximal portions 540/540' have, are directly proportional to the outwardly and/or radial force of the proximal portions 540/540' of the devices when transition from the delivery constrained configuration to the deployed expanded configuration. For example, the proximal portion 540 of FIGS. 10-11C having connectors 555 in substantially all or at least most of the respective points, sections or areas where the undulating elements 150 contact each other, is configured to have a larger outward and/or radial force (e.g., during expansion to the deployed expanded configuration) than the proximal portion 540' of FIG. 17 having some or selected connector 555. Additionally, the location and/or quantity of the connector 555 in the proximal portion 540' may be selected depending on the desirable outward and/or radial force for expansion of the proximal portion 540' when deployed. Exemplary methods of use of the embolectomy devices and radial forces exerted during expansion will be described in further detail below.

Additionally to the connectors 555 of the proximal portion 540 of the device 500, a connector 557 is disposed between the proximal 540 and distal 580 portions of the device 500, as shown in FIG. 10. The connector 557 comprise direct or indirect coupling, attachment or securement, such as, by adhesive, thermal bonding, welding, interlocking geometries, mechanical fastening, or the like or combinations thereof. The connector 557 is centrally disposed (e.g., intersecting or close to axis 530) and is configured to reduce the range of motion between the respective distal portions 180 relative to each other. Alternatively, the connector 557 may be disposed at any location between the proximal 540 and distal 580 portions of the device 500. In some embodiments, the device 500 may not include the connector 557, so that the range of motion between the respective distal portions 180 relative to each other is larger than the range of motion when the device 500 includes the connector 557. In other embodiments and by way of non-limiting example, some embolectomy devices may be coupled to each other at the proximal ends 125 only (e.g., via wire 444), or the devices may be coupled at the proximal ends 125 and at their respective proximal and distal portions (e.g., connector 557) without having any connector 555 therebetween (not shown).

Referring back to FIG. 10, the embolectomy device 500 is further coupled to an elongate wire 444; the wire 444 is configured to advance and withdraw the embolectomy device 500 through sheaths and/or catheters into a target site in a blood vessel. As shown in FIG. 10, the respective proximal ends 125 of each of the clot engaging devices 100 forming the embolectomy device 500 are coupled, attached or secured to the wire 444 by solder, weld, adhesive, or other suitable attachment methods. The attachment of the respective proximal ends 125 to the wire 444 is also configured to secure the respective proximal portions 140 forming the proximal portion 540 of the device 500 with respect to each other.

FIG. 10B is a side (profile) view, seen from the cross-sectional plane of the distal portion 580 of the device 500 at FIG. 10 viewed towards a distal end 582, as indicated by arrows "B1". The arcuate expanded configurations of the respective clot engaging devices 100 are configured to face inwardly (e.g., concave surface facing inwardly 182) at the distal portion 580 of the device 500. The distal portions 180 of the respective clot engaging devices 100 forming the device 500 are not coupled to each other, allowing the distal portions 180 to move relative to each other in the expanded configuration of the device 500. Thus, the distal portion 580 of the device 500 comprises a variable expanded outer diameter (EOD) (shown in dashed lines in FIG. 10B) configured expand and contact the vessel walls of a variety of sized blood vessels. It should be appreciated that since the distal portions 180 of the respective clot engaging devices 100 are not coupled to each other, the outward and/or radial force of the distal portion 580 of the device 500 (e.g., during expansion to the deployed expanded configuration) is smaller than the outward and/or radial force exerted by the proximal portion 540 or 540' of the device 500.

Figure 11A:
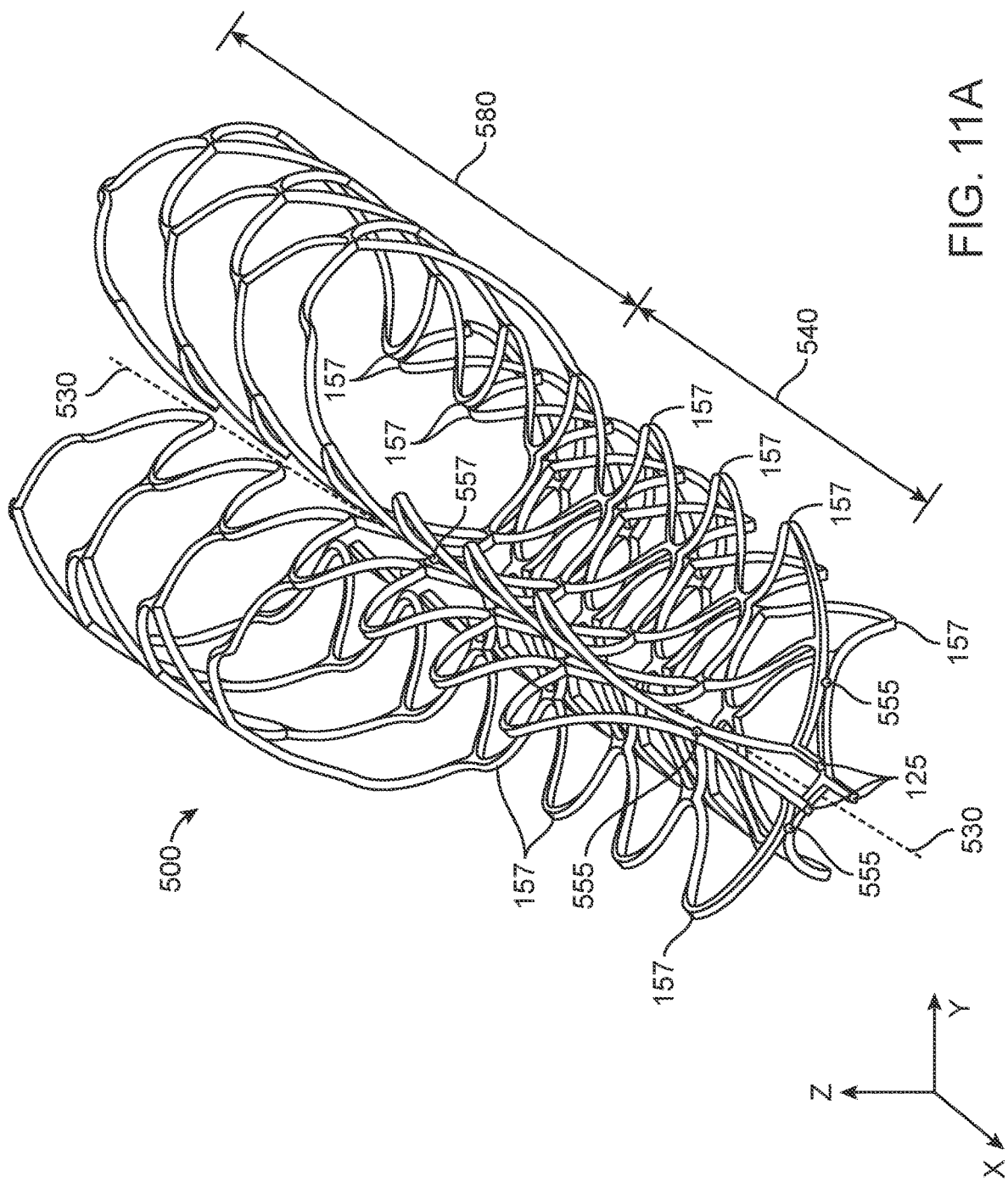
FIGS. 11A-11C are additional perspective views of the embolectomy device of FIGS. 10, 10A-10B.
Figure 11B:
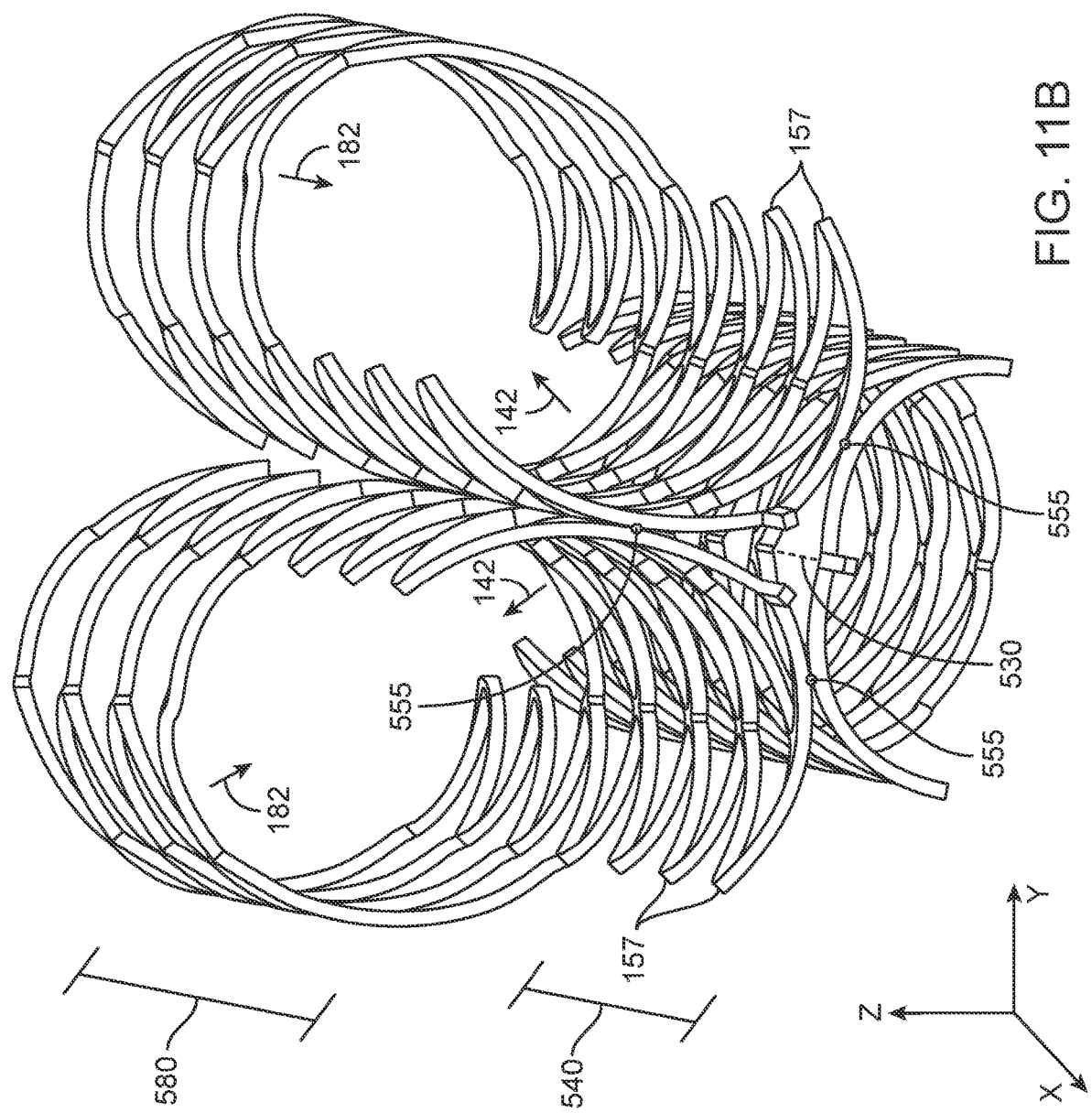
Figure 11C:
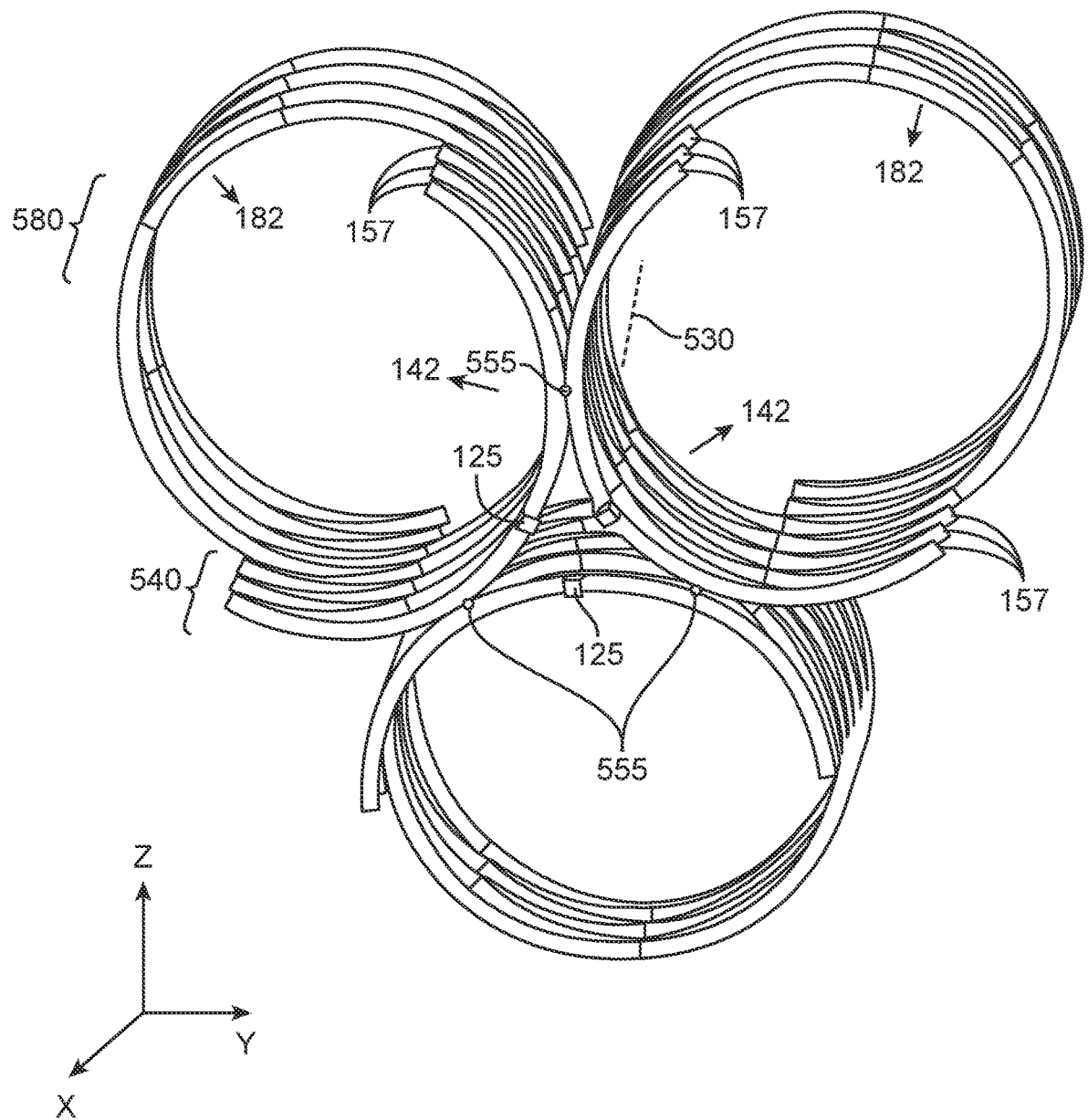

FIGS. 11A-C depict the embolectomy device 500 of FIGS. 10 and 10A-B in perspective three-dimensional views of the device expanded configuration. FIGS. 11A-C depict the embolectomy device 500 as having the proximal ends 125 of the clot engaging devices 100 further translated along the y-axis in the 3D Cartesian coordinate system. The arcuate expanded configuration of the respective proximal portion 140 (e.g., concave surfaces facing outwardly) forming the proximal portion 540 of the device 500, outline or contour the "fin-like" configuration of the maximum/peak regions 157 of respective elements 150, as previously described in FIGS. 5A-C. The expanded proximal portion 540 of the device 500 comprises arcuate configuration forming three pairs of "fin-like" configuration, as shown in FIGS. 11A-C. The arcuate expanded configuration of the respective distal portions 180 (e.g., concave surfaces facing inwardly) forming the distal portion 580 of the embolectomy device 500 outline or contour three adjacently semicircular profiles disposed around the central axis 530 of the embolectomy device 500 (FIGS. 10B and 11A-C).

FIGS. 12, 12A-B, and 13A-C illustrate an embolectomy device 600, constructed in accordance with embodiments of the disclosed inventions. For ease in illustration, the features, functions, and configurations of the embolectomy device 600 of FIGS. 12, 12A-B, and 13A-C that are the same as in the embolectomy device 500 of FIGS. 10, 10A-B, and 11A-C are given the same reference numerals. The embolectomy device 600 comprises a plurality of embolectomy devices 200 of FIGS. 6 and 7A-C. FIG. 12 depicts the embolectomy device 600 having three embolectomy devices 200 coupled to each other in a "back-to-back" expanded configuration, as better appreciated in FIGS. 12A-B, 13A-C. The embolectomy device 600 includes a proximal portion 640, a distal portion 680, and a central axis 630 extending therebetween. Each of the embolectomy devices 200 forming the embolectomy device 600 comprises a plurality of longitudinal undulating elements 150 (e.g., wires, struts, bundle of wires, drawn-filled tubes, or the like) having respective sinusoid configurations so that adjacently disposed undulating elements 150 form a plurality of adjacently disposed cells 160. As previously disclosed in FIGS. 6 and 6A, each of the embolectomy devices 200 includes elongated elements 250 coupled to the outwardly disposed undulating elements 150 forming respective cells 260. Further, the undulating elements 150, connection points 155 between the elements 150, and cells 160 of the respective proximal portions 240 of the devices 200 are symmetrically disposed with a respect to their respective central axis 130.

Figure 13B:
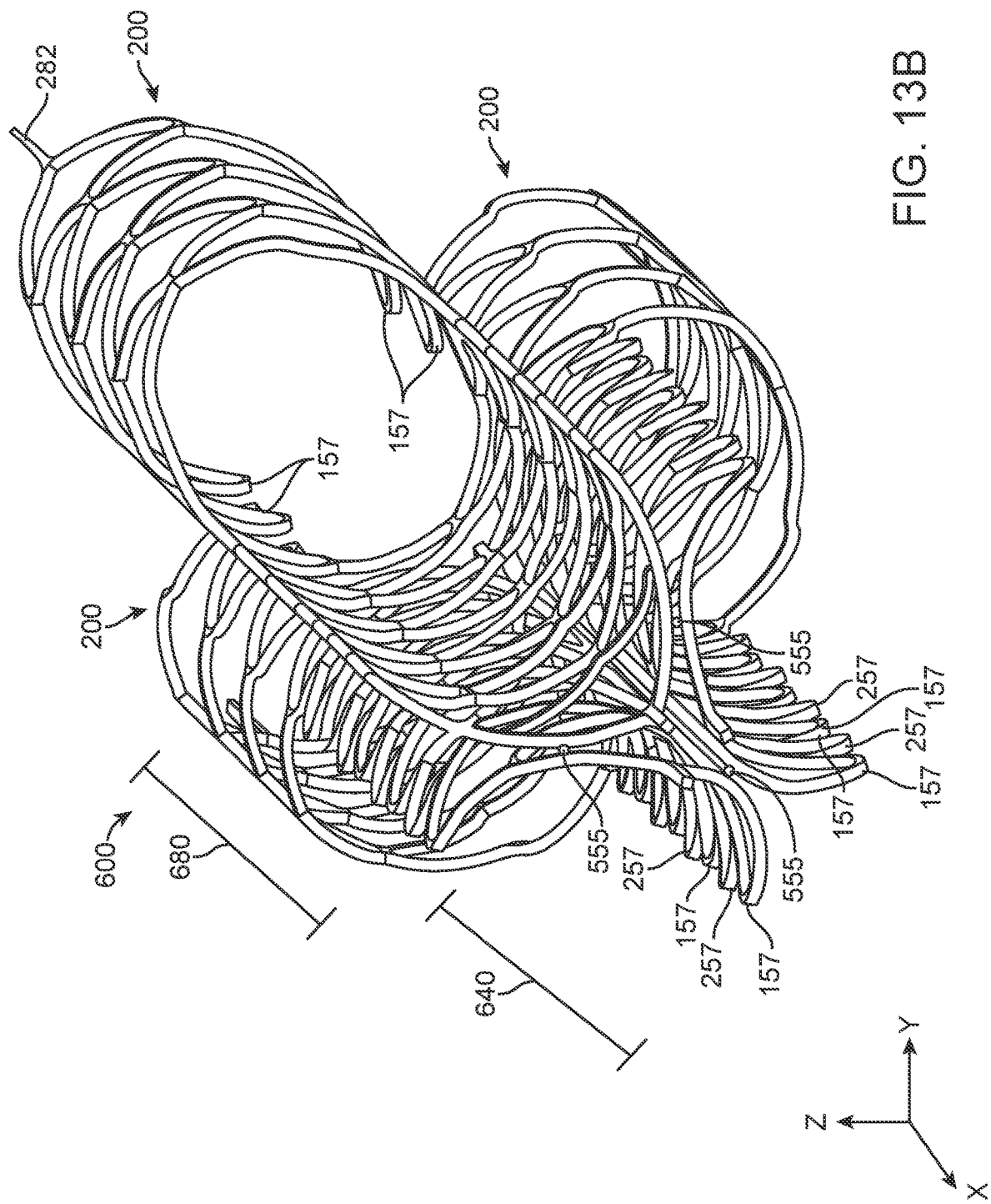
Figure 13C:
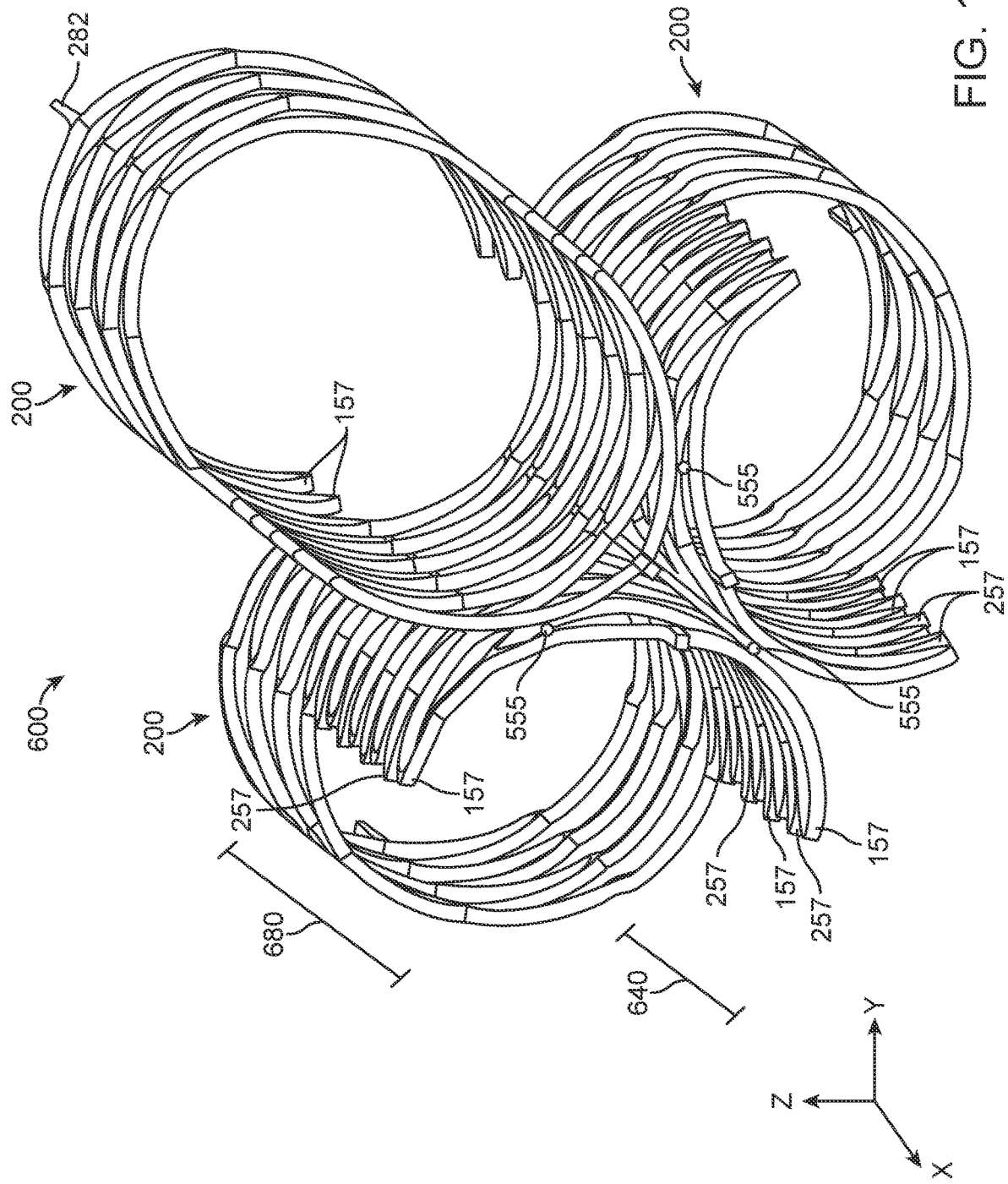

Similar to the device 500 of FIGS. 10-11C, the embolectomy device 600 of FIGS. 12-13C has an overall length L9 of approximately 30 millimeters with the proximal portion 640 length L10 measuring approximately between 10 to 20 millimeters. In the embodiment of FIG. 12, the proximal portion 640 and the distal portion 680 have approximately the same length. In some embodiments, the length of the proximal portion 640 is generally between 0.5 to 3.5 times greater than the length of the distal portion 680, as shown in exemplary embodiment of FIG. 18. In an unexpanded or radially compressed configuration (not shown), the embolectomy device 500 has an unexpanded outer diameter (UOD) between 0.4 to 0.7 millimeters. In a radially expanded configuration (FIGS. 12-13C), the proximal portion 640 of the embolectomy device 600 comprises an expanded outer diameter (EOD) between 1.5 to 5.0 millimeters, and the distal portion 680 comprises an expanded outer diameter (EOD) between 1.5 to 6.0 millimeters.

The embolectomy device 600 is shown in a perspective side view of the expanded configuration in FIG. 12, such as having respective proximal ends 125 of each of the devices 200, and the central axis 630 of the device 600 disposed parallel to the x-axis in the 3D Cartesian coordinate system. Each of the proximal portions 240 of the devices 200 are coupled, attached or secured to each other forming embolectomy device 600. Due to the symmetry of the undulating elements 150, connection points 155 between the elements 150, and cells 160 of the respective proximal portions 240 of the device 200, some points, sections or areas of the undulating elements 150 of one of the device 200 are configured to contact respective points, sections or areas of the undulating elements 150 of the other two adjacently disposed devices 200 in a "back-to-back" configuration. As better appreciated in the side (profile) view of FIG. 12A, seen from the cross-sectional plane of the proximal portion 640 of the device 600 at FIG. 12 viewed towards the proximal ends 125, as indicated by arrows "A1", the respective points, sections or areas of undulating elements 150 are coupled, attached or secured by connectors 555 to respective adjacent undulating elements 150. The connectors 555 comprise direct or indirect coupling, attachment or securement, such as, by adhesive, thermal bonding, welding, interlocking geometries, mechanical fastening, or the like or combinations thereof. The arcuate expanded configurations of the respective devices 200 are configured to face outwardly (e.g., concave surface facing outwardly) in the proximal portion 640 of the device 600, as shown in FIG. 12A. When the device 600 expands from the constricted configuration, the respective arcuate configuration of the devices 200 produce sufficient outwardly and/or radial force (e.g., radial force per unit length of between 0.005 N/mm to 0.050 N/mm, preferable between 0.030 N/mm to 0.050 N/mm) to snare, engage and/or otherwise capture an obstruction in the vasculature, as it will be described in further detail below.

It should be appreciated that the proximal portion 640 of the device 600 may include connectors 555 in all, substantially all, most (FIGS. 12-13C) or in selectively some (not shown; similar to FIG. 17) of the respective points, sections or areas where the undulating elements 150 contact each other. The quantity of connectors 555 that the proximal portion 640 has, is directly proportional to the outwardly and/or radial force of the proximal portion 640 of the device 600 when transition from the delivery constrained configuration to the deployed expanded configuration. Additionally, the location and/or quantity of the connector 555 in the proximal portion 640 may be selected depending on the desirable outward and/or radial force for expansion of the proximal portion 640 when deployed. Exemplary methods of use of the embolectomy devices and radial forces exerted during expansion will be described in further detail below.

Additionally to the connectors 555 of the proximal portion 640 of the device 600, and similar to the device 500 of FIGS. 10-11C, connector 557 is disposed between the proximal 640 and distal 680 portions of the device 600, as shown in FIG. 12. The connector 557 comprise direct or indirect coupling, attachment or securement, such as, by adhesive, thermal bonding, welding, interlocking geometries, mechanical fastening, or the like or combinations thereof. The connector 557 is centrally disposed (e.g., intersecting or close to axis 630) and is configured to reduce the range of motion between the respective distal portions 280 relative to each other. Alternatively, the connector 557 may be disposed at any location between the proximal 640 and distal 680 portions of the device 600. In some embodiments, the device 600 may not include the connector 557, so that the range of motion between the respective distal portions 280 relative to each other is larger than the range of motion when the device 600 includes the connector 557.

Similarly the device 500 of FIGS. 10-11C, the embolectomy device 600 of FIGS. 12-13C is coupled to an elongate wire 444; the wire 444 is configured to advance and withdraw the embolectomy device 600 through sheaths and/or catheters into a target site in a blood vessel. As shown in FIGS. 12 and 13-A, the respective proximal ends 125 of each of the clot engaging devices 100 forming the embolectomy device 600 are coupled, attached or secured to the wire 444 by solder, weld, adhesive, or other suitable attachment methods. The attachment of the respective proximal ends 125 to the wire 444 is also configured to secure the respective proximal portions 240 forming the proximal portion 640 of the device 600 with respect to each other.

FIG. 12B is a side (profile) view, seen from the cross-sectional plane of the distal portion 680 of the device 600 at FIG. 12 viewed towards the distal antennas 282, as indicated by arrows "B1". The arcuate expanded configurations of the respective devices 200 are configured to face inwardly (e.g., concave surface facing inwardly) at the distal portion 680 of the device 600. The distal portions 280 of the respective devices 200 forming the device 600 are not coupled to each other, allowing the distal portions 280 to move relative to each other in the expanded configuration of the device 600. Thus, the distal portion 680 of the device 600 comprises a variable expanded outer diameter (EOD) (shown in dashed lines in FIG. 12B) configured expand and contact the vessel walls of a variety of sized blood vessels. It should be appreciated that since the distal portions 280 of the respective devices 200 are not coupled to each other, the outward and/or radial force of the distal portion 680 of the device 600 (e.g., during expansion to the deployed expanded configuration) is smaller than the outward and/or radial force exerted by the proximal portion 640 of the device 600.

FIGS. 13A-C depict the embolectomy device 600 of FIGS. 12 and 12A-B in perspective three-dimensional views of the device expanded configuration. FIGS. 13A-C depict the embolectomy device 600 as having the proximal ends 125 of the devices 200 further translated along the y-axis in the 3D Cartesian coordinate system. The arcuate expanded configuration of the respective proximal portion 240 (e.g., concave surfaces facing outwardly) forming the proximal portion 640 of the device 600, outline or contour the "fin-like" configuration of the maximum/peak regions 157 of respective elements 150 and the maximum/peak regions 257 of respective elements 250, as previously described in FIGS. 6, 6A and 7A-C. The expanded proximal portion 640 of the device 600 comprises arcuate configuration forming three pairs of "fin-like" configuration, as shown in FIGS. 13A-C. The arcuate expanded configuration of the respective distal portions 280 (e.g., concave surfaces facing inwardly) forming the distal portion 680 of the device 600 outline or contour three adjacently semicircular profiles disposed around the central axis 630 of the device 600 (FIGS. 12B and 13A-C).

Additionally, FIGS. 12 and 13A-C depicts the distal portion 680 of the device 600 formed by respective distal portions 280 having elongated distal ends or antennas 282. In some embodiments, the respective elongated distal ends or antennas 282 the distal portion 680 are coupled to each other and a coil 284 is disposed over and/or around the joined antennas 282 in the expanded configuration of the device 600, as shown FIG. 12C. The coil 284 may include a non-traumatic tip 285 and composed of radio-opaque material. It should be appreciated that the coil 284 may be disposed over one of the single antennas 282, or two joined antennas 282, or combination thereof. Additionally, the antennas 282 may have a variety of length and/or may be off-set before the coil 284 is disposed, such as to create less mass/volume when the antennas 282 are coupled to each other. In alternative embodiments, the antennas 282 may be coated with radiopaque materials, include a clamp, or any other radiopaque marker. It should be appreciated that the embolectomy devices of FIGS. 4-19 may further include elongated distal ends or antennas and markers, similar to the antennas 282 and coil 284 of FIGS. 6-7C and 12-13C.

FIGS. 14 and 14A illustrate an embolectomy device 700, constructed in accordance with embodiments of the disclosed inventions. The embolectomy device 700 comprises a plurality of embolectomy devices 300 of FIG. 8. FIG. 14 depicts the embolectomy device 700 having three embolectomy devices 300 coupled to each other in a "back-to-back" expanded configuration, as better appreciated in FIG. 14A. The embolectomy device 700 includes a body portion 740, similar to the proximal portion 540 of the device 500. Each of the embolectomy devices 300 forming the embolectomy device 700 comprises a plurality of longitudinal undulating elements 150 (e.g., wires, struts, bundle of wires, drawn-filled tubes, or the like) having respective sinusoid configurations so that adjacently disposed undulating elements 150 form a plurality of adjacently disposed cells 160. The undulating elements 150, connection points 155 between the elements 150, and cells 160 of the respective body portions 340 of the devices 300 are symmetrically disposed, as previously disclosed in FIG. 8. The embolectomy device 700 has an overall length L11 of approximately 30 millimeters.

The embolectomy device 700 is shown in a perspective side view of the expanded configuration in FIG. 14, such as having respective proximal ends 125 of each of the devices 300, and a central axis 730 of the device 700 disposed parallel to the x-axis in the 3D Cartesian coordinate system. Each of the body portions 340 of the devices 300 are coupled, attached or secured to each other forming embolectomy device 700. Due to the symmetry of the undulating elements 150, connection points 155 between the elements 150, and cells 160 of the respective body portions 340 of the devices 300, some points, sections or areas of the undulating elements 150 of one of the device 300 are configured to contact respective points, sections or areas of the undulating elements 150 of the other two adjacently disposed devices 300 in a "back-to-back" configuration. As better appreciated in the side (profile) view of FIG. 14A, seen from the cross-sectional plane of the body portion 740 of the device 700 at FIG. 14 viewed towards the proximal ends 125, as indicated by arrows "A1", the respective points, sections or areas of undulating elements 150 are coupled, attached or secured by connectors 555 to respective adjacent undulating elements 150. The connectors 555 comprise direct or indirect coupling, attachment or securement, such as, by adhesive, thermal bonding, welding, interlocking geometries, mechanical fastening, or the like or combinations thereof. The arcuate expanded configurations of the respective devices 300 are configured to face outwardly (e.g., concave surface facing outwardly) in the body portion 740 of the device 700, as shown in FIG. 14A. It should be appreciated that the body portion 740 of the device 700 may include connectors 555 in all, substantially all, most or selectively in some (not shown) of the respective points, sections or areas where the undulating elements 150 contact each other in a "back-to-back" configuration, as previously described.

When the device 700 expands from the constricted configuration, the respective arcuate configuration of the devices 700 produce sufficient outwardly and/or radial force (e.g., radial force per unit length of between 0.005 N/mm to 0.050 N/mm, preferable between 0.030 N/mm to 0.050 N/mm) to snare, engage and/or otherwise capture an obstruction in the vasculature, as it will be described in further detail below. The embolectomy device 700 may be used in combination with a distal filter or protection (not shown). The embolectomy device 700 is further coupled to elongate wire 444 configured to advance and withdraw the embolectomy device through sheaths and/or catheters into a target site in a blood vessel, as previously described.

FIGS. 15 and 15A illustrate an alternative embodiment of the embolectomy device of FIGS. 12 and 12A, constructed in accordance with the disclosed inventions. For ease in illustration, the features, functions, and configurations of an embolectomy device 800 of FIGS. 15 and 15A that are similar or the same as in the previously disclosed device 600 of FIGS. 12-13C, are given the same reference numerals, and the above disclosure is incorporated by reference herein. The embolectomy device 800 of FIGS. 15 and 15A includes a body portion 840 substantially similar to the proximal portion 640 of the device 600 of FIGS. 12 and 12A. Similar to the proximal portion 640 of the device 600 of FIG. 12, the body portion 840 of the device 800 (FIG. 15) is formed by having three structures similar to the proximal portions 240 of devices 200 (FIG. 6) coupled to each other in a "back-to-back" expanded configuration. One difference with the device 600 of FIG. 12 is that the embolectomy device 800 of FIG. 15 does not include a distinct distal portion (e.g., 680); instead the body portion 840 of the device 800 (e.g., longer proximal portion 640) extends along the overall length L13 of the device, as shown in FIG. 15. The overall length L13 of the body portion 840 of the device 800 is approximately 30 millimeters.

The embolectomy device 800 is shown in a perspective side view of the expanded configuration in FIG. 15, such as having respective proximal ends 125 and a central axis 830 of the device 800 disposed parallel to the x-axis in the 3D Cartesian coordinate system. The embolectomy device 800 comprises a plurality of longitudinal undulating elements 150 (e.g., wires, struts, bundle of wires, drawn-filled tubes, or the like) having respective sinusoid configurations so that adjacently disposed undulating elements 150 form a plurality of adjacently disposed cells 160. Further, the embolectomy device 800 of FIG. 15 includes elongated elements 250 coupled to outwardly disposed undulating elements 150, forming respective cells 260, similar to FIG. 6 and FIG. 12. The undulating elements 150, connection points 155 between the elements 150 and cells 160 are symmetrically disposed, as shown in FIG. 15, and as previously disclosed for the proximal portions of FIGS. 6 and 12. Due to the symmetry of the undulating elements 150, connection points 155 between the elements 150, and cells 160, some points, sections or areas of the undulating elements 150 are configured to contact respective points, sections or areas of the undulating elements 150 in a "back-to-back" configuration.

As better appreciated in the side (profile) view of FIG. 15A, seen from the cross-sectional plane of the body portion 840 of the device 800 at FIG. 15 viewed towards the proximal ends 125, as indicated by arrows "A1", the respective points, sections or areas of undulating elements 150 are coupled, attached or secured by connectors 555 to respective adjacent undulating elements 150. The connectors 555 comprise direct or indirect coupling, attachment or securement, such as, by adhesive, thermal bonding, welding, interlocking geometries, mechanical fastening, or the like or combinations thereof. The respective arcuate expanded configurations of the body portion 840 of the device 800 are configured to face outwardly (e.g., concave surface facing outwardly), as shown in FIG. 15A. It should be appreciated that the body portion 840 of the device 800 may include connectors 555 in all, substantially all, most (FIGS. 15-15C), or in some (not shown) of the respective points, sections or areas where the undulating elements 150 contact each other in a "back-to-back" configuration, as previously described.

When the device 800 expands from the constricted configuration, the respective arcuate configuration of the devices 800 produce sufficient outwardly and/or radial force (e.g., radial force per unit length of between 0.005 N/mm to 0.050 N/mm, preferable between 0.030 N/mm to 0.050 N/mm) to snare, engage and/or otherwise capture an obstruction in the vasculature, as it will be described in further detail below. The embolectomy device 800 may be used in combination with a distal filter or protection (not shown). The embolectomy device 800 is further coupled to elongate wire 444 configured to advance and withdraw the embolectomy device through sheaths and/or catheters into a target site in a blood vessel, as previously described.

Figure 16A:
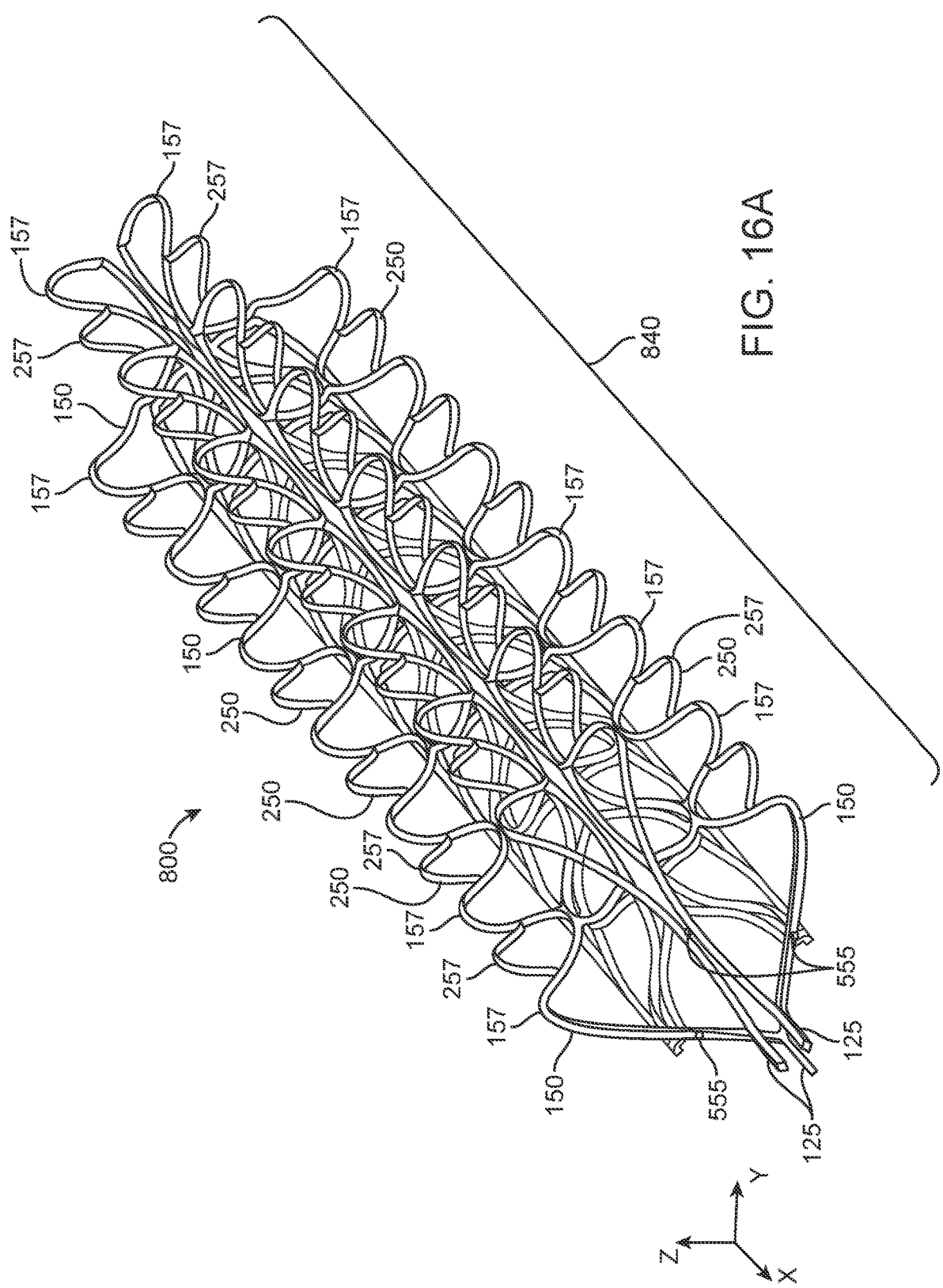
FIGS. 16A-16C are perspective views of the embolectomy device of FIGS. 15, 15A.
Figure 16B:
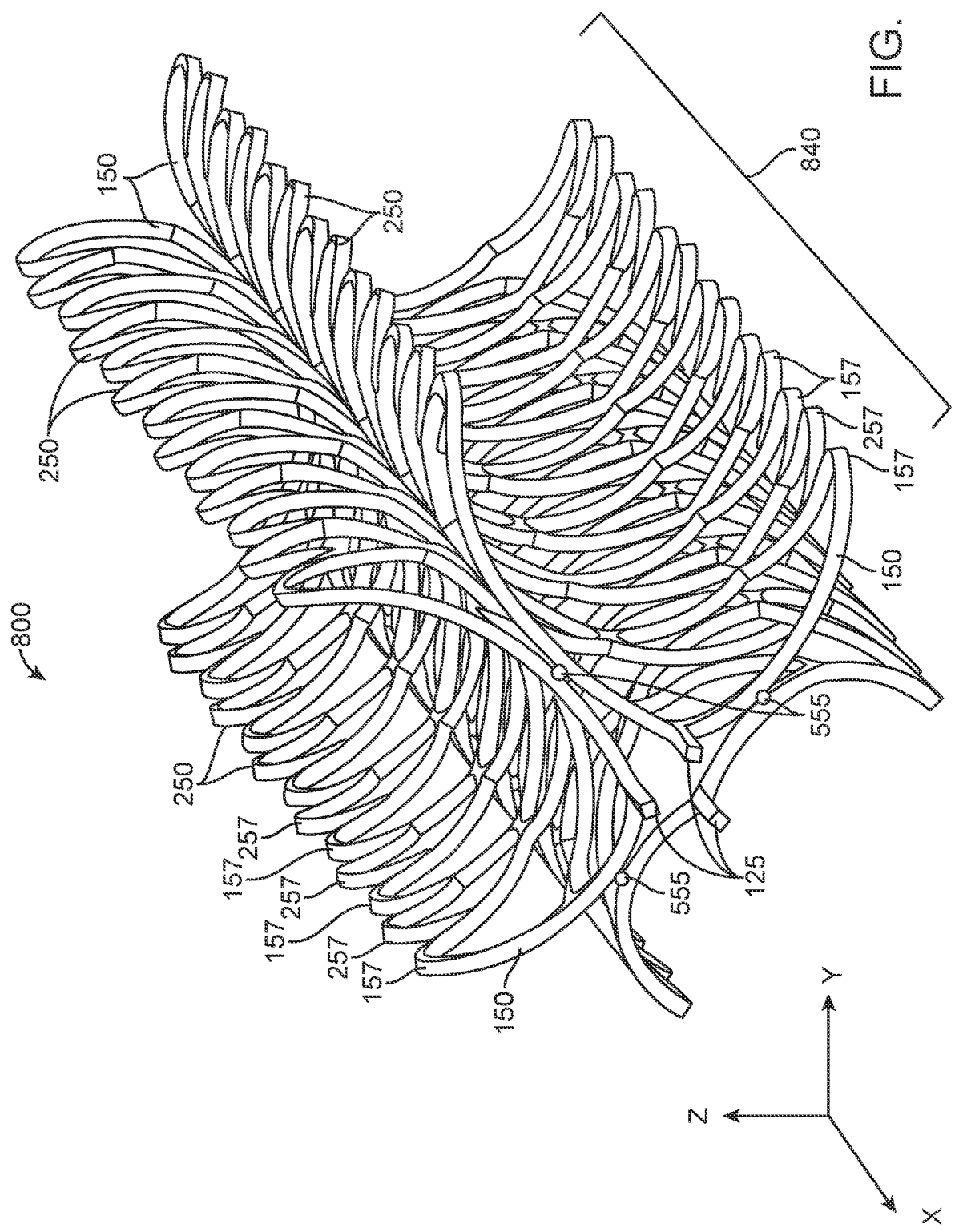
Figure 16C:
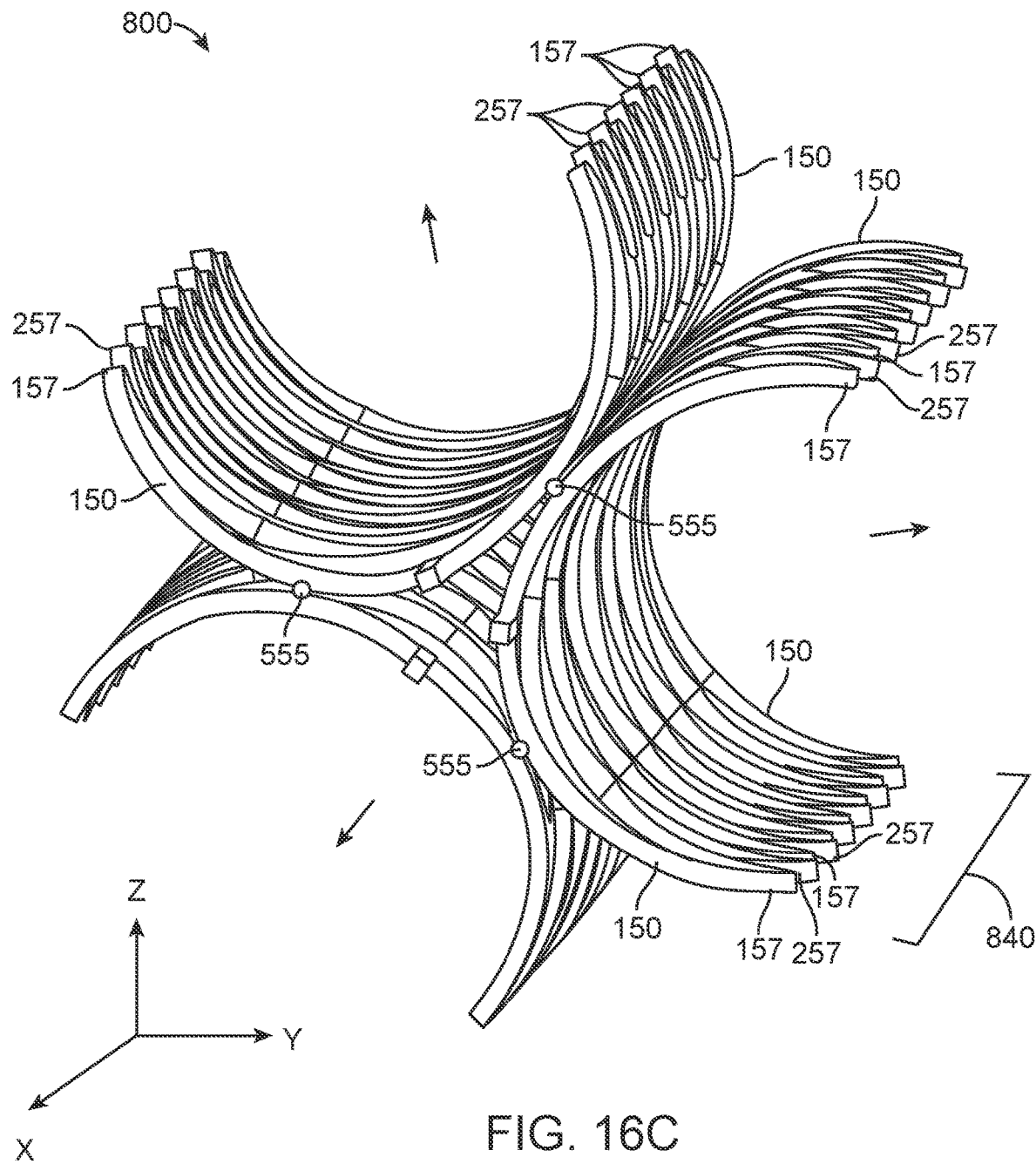

FIGS. 16A-C depict the embolectomy device 800 of FIGS. 15 and 15A in perspective three-dimensional views of the device expanded configuration. FIGS. 16A-C depict the embolectomy device 800 as having the proximal ends 125 further translated along the y-axis in the 3D Cartesian coordinate system. The arcuate expanded "back-to-back" configuration (e.g., concave surfaces facing outwardly) forming the proximal portion 840 of the device 800, outline or contour the "fin-like" configuration of the maximum/peak regions 157 of respective elements 150 and the maximum/peak regions 257 of respective elements 250, as previously described (e.g., for the proximal portions in FIGS. 6, 6A and 7A-C). The expanded body portion 840 of the device 800 comprises arcuate configuration forming three pairs of "fin-like" configuration, as shown in FIGS. 16A-C.

Figure 18:
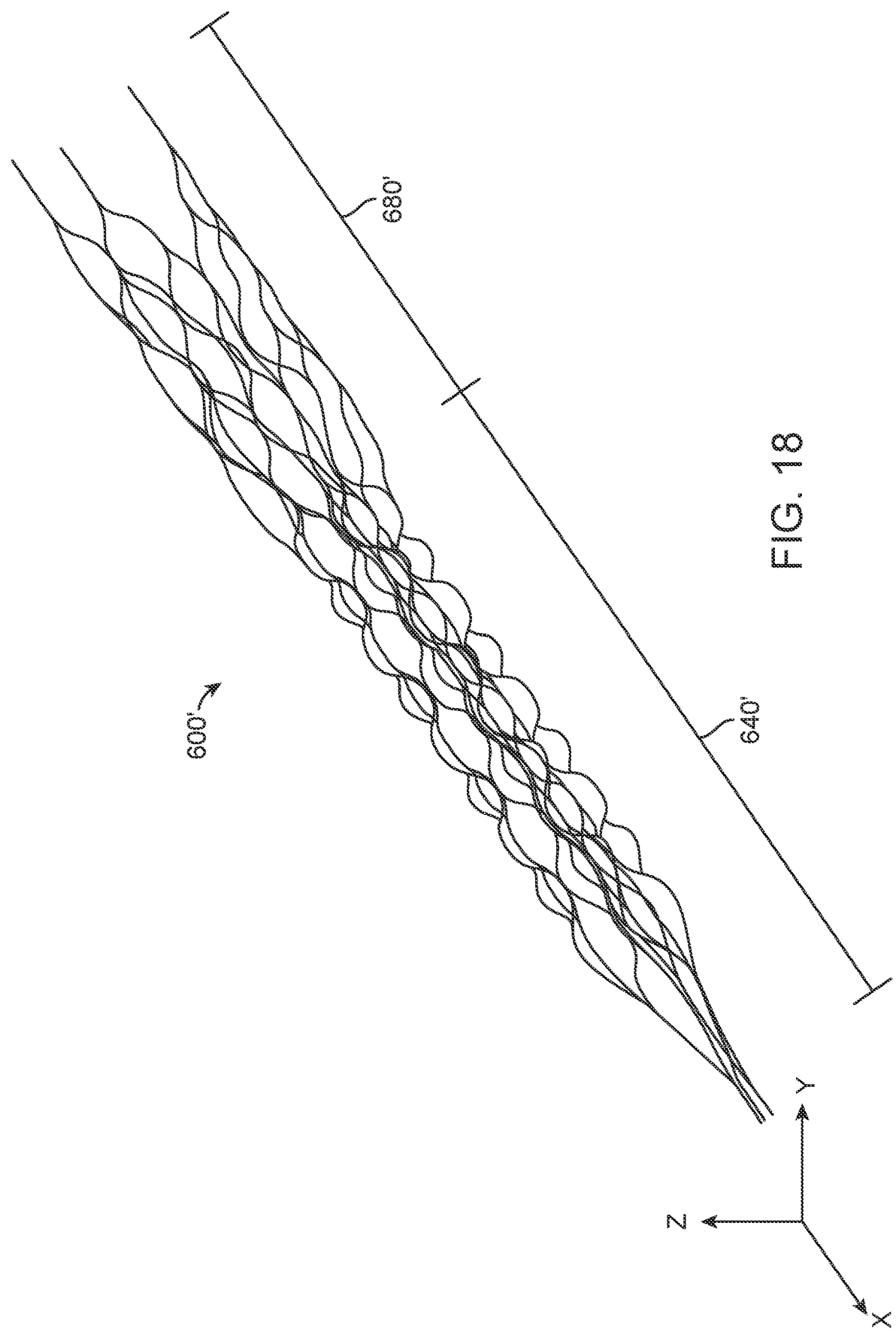
FIG. 18 is a perspective view of an embolectomy device having alternative proximal and distal portions, constructed according embodiments of the disclosed inventions.

FIG. 18 illustrates an alternative embodiment of the embolectomy device 600 of FIGS. 12-13C. For ease in illustration, the features, functions, and configurations of an embolectomy device 600' of FIG. 18 that are similar or the same as in the previously disclosed device 600 of FIGS. 12-13C, are given the same reference numerals and the above disclosure is incorporated by reference herein. The embolectomy device 600' of FIG. 18 is substantially similar to the device 600 of FIGS. 12-13C with the main difference being that the device 600' has different lengths between the proximal portion 640 and distal portion 680. As shown in FIG. 18, the proximal portion 640 is longer than the distal portion 680 in the device 600'. It should be appreciated that the length of the proximal portion 640 may be generally between 0.5 to 3.5 times greater than the length of the distal portion 680 in the device 600'. Although FIG. 18 is an alternative embodiment of the device of FIGS. 12-13C, it should be appreciated that any of the previously disclosed clot engaging devices 100, 200, 300 and 400, as well as the embolectomy device 500, having distinct proximal and distal portions may have a longer proximal portion relative to the respective distal portion, as shown for example in FIG. 18.

FIG. 19 illustrates an alternative embodiment 500" of the embolectomy device 500 of FIGS. 10-11C. For ease in illustration, the features, functions, and configurations of an embolectomy device 500" of FIG. 19 that the same or similar as in the previously disclosed device 500 of FIGS. 10-11C, are given the same reference numerals and the above disclosure is incorporated by reference herein. The embolectomy device 500" of FIG. 19 is substantially the same as device 500 of FIGS. 10-11C with the main difference being that the device 500" further includes one or more elongate members 350 (e.g., filaments, suture, fibers, threads, wires, or the like) that are coupled, attached or secured to the embolectomy device 500". The elongate members 350 are coupled to the undulating elements 150 of the device 500" by a solder, weld, adhesive, be being woven into the device or by any other suitable attachment methods. In one embodiment, a single elongated member 350 is woven along the length L7 of the proximal portion 540 (not shown). In the embodiment of FIG. 19, multiple elongate members 350 are coupled to selective undulating members 150.

As better appreciated in the side (profile) view of FIG. 19A, seen from the cross-sectional plane of the proximal portion 540 of the device 500" at FIG. 19 viewed towards the proximal ends 125, as indicated by arrows "A1", the respective points, sections or areas of undulating elements 150 are coupled by connectors 555 to respective adjacent undulating elements 150, as previously described in FIGS. 10-11C. As shown in FIG. 19A, the elongate members 350 coupled to the undulating elements 150 are disposed within the respective arcuate concave surfaces facing outwardly of the proximal portion 540. Although the elongate members 350 are shown approximately symmetrically disposed in the cross-sectional plane view of FIG. 19A, it should be appreciated that the elongate members 350 may be non-symmetrically disposed, as shown along the length of the proximal portion 540 in FIG. 19. The elongate members 350 are configured to increase the mass, volume and/or contact structures of the embolectomy devices, assisting with the engagement, retention and/or retrieval of the obstruction. In some embodiments, further elongate members 350 are be disposed in the distal portion 580 of the device 500" (not shown). Although FIG. 19 is an alternative embodiment of the device of FIGS. 10-11C, it should be appreciated that one or more the elongate members 350 may be coupled to any portion (e.g., proximal, distal, body) of the previously disclosed embolectomy devices (FIGS. 4-9 and FIGS. 12-18).

FIGS. 20A-D illustrate an exemplary use of the embolectomy devices according to the disclosed inventions. The exemplary embolectomy procedure depicted in FIGS.

Figure 20A:
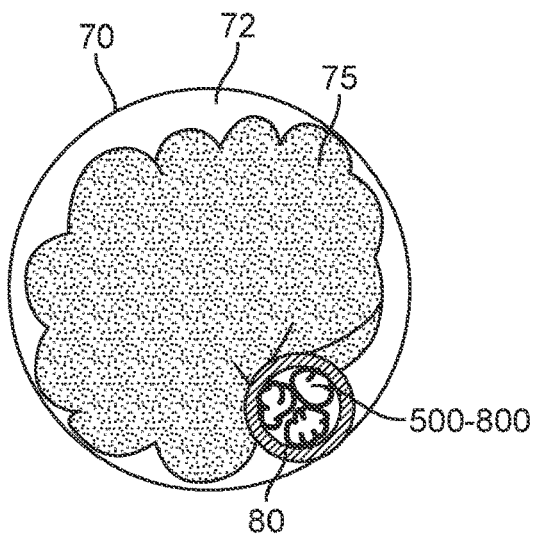
FIGS. 20A-20D are cross-sectional views of the any of the embolectomy devices of FIGS. 10-19, shown disposed within a blood vessel adjacent to an embolic obstruction.

20A-D may use any of the embolectomy devices 500-800 (FIGS. 10-19) having at least three sets of arcuate configurations with arcuate concave surfaces facing outwardly, as previously described above. FIGS. 20A-D are cross-sectional views of the blood vessel 70 having lumen 72 with the embolic obstruction 75 therein. In the embolectomy procedure for removing the embolic obstruction 75 from the blood vessel lumen 72, the delivery catheter 80 is advanced through the lumen 72, until the distal portion of the catheter 80 is disposed in a target site adjacent to the obstruction 75, with the radially compressed embolectomy device 500-800 disposed within the catheter 80, as shown in FIG. 20A.

Figure 20B:
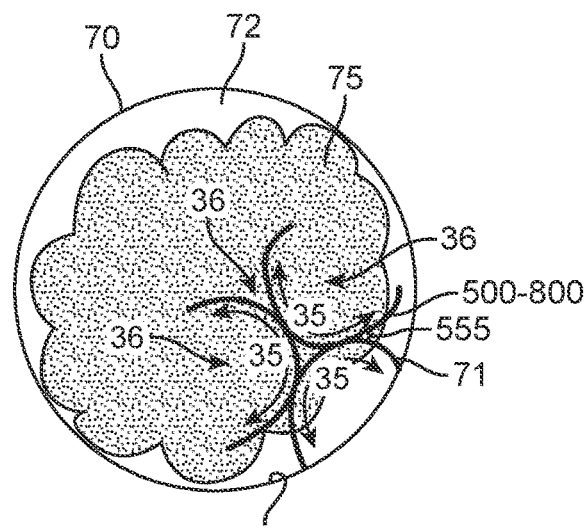
Figure 20C:
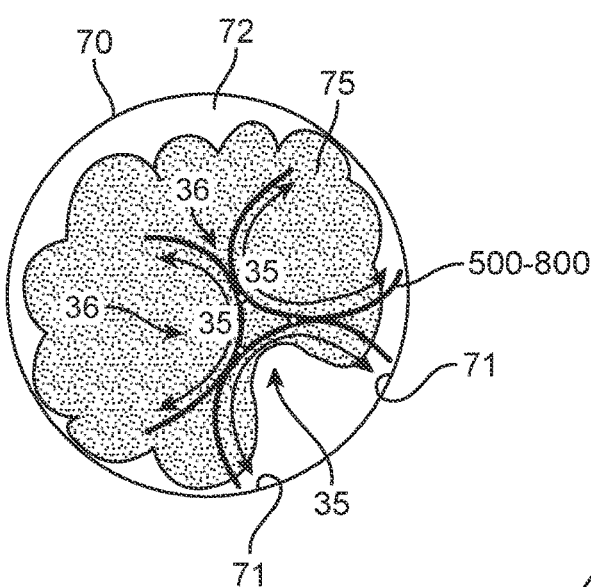
Figure 20D:
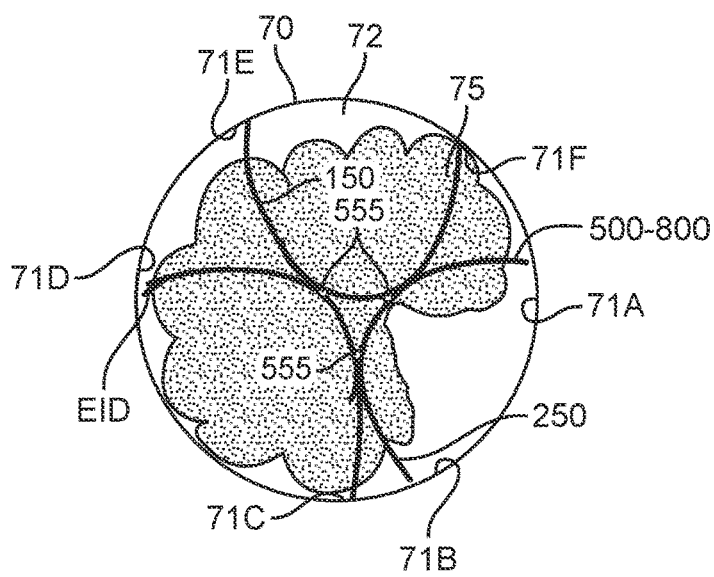

The embolectomy device 500-800 is either pushed distally relative to the catheter 80 or the catheter 80 is withdrawn proximally relative to the embolectomy device 500-800, or some of each (not shown), in order to deploy the device 500-800 out of the catheter 80 and into the blood vessel lumen 72, and further allow the no-longer radially constrained embolectomy device 500-800 to radially expand within the blood vessel lumen 72, so as to engage, ensnare and capture the obstruction 75. The sets of arcuate configurations having concave surfaces facing outwardly in their respective proximal portions, allows, assists and/or supports the radial expansion forces 33 of the embolectomy devices 500-800, and further assist the device 500-800 to overcome the resistive forces 36 of the embolic obstruction 75, which in turn allows the device 500-800 to penetrate and integrate the obstruction 75, as shown in FIGS. 20C-D.

The radial strength along the length of the embolectomy device may be varied in a variety of ways. One method is to vary the mass (e.g., width and/or thickness) of the undulating elements 150, elongate elements 250, and/or elongate members 350 along the length of the device 500-800. In the embodiments of FIGS. 10-19, the at least three sets of arcuate configurations with arcuate concave surfaces facing outwardly of the devices 500-800 are mainly configured to be the active portion of their respective devices, for engagement, ensnaring or otherwise, capturing embolic obstructions or clots in the vasculature of a patient. It should be appreciated that other portions of the devices 500-800 may also actively engage, integrate and/or retain embolic obstructions, such as for example, the distal portions 580/680. Another method is to vary the number and/or size of the cells along the length of the embolectomy devices, such as having additional cells 260 shown in the exemplary device 600 of FIGS. 12-13C. The use of smaller cell will generally provide higher radial forces than those that are larger. Varying the radial force exerted along the length of the embolectomy devices can be particularly advantageous for use in entrapping and retrieving embolic obstructions.

For example, in the embodiments of FIGS. 10-11C and 12-13C the radial force exerted by the proximal portions 540/640 (e.g., active portion) when expanded, is configured to be greater than the radial force exerted by the distal portions 580/680 of the respective devices 500/600. The configuration of the sets of arcuate concave surfaces facing outwardly of the devices of FIGS. 10-11C and 12-13C promote a larger radial force of their respective proximal portions into the embolic obstructions than the radial force of their distal portions. In some embodiments, the radial force exerted by the arcuate configurations with arcuate concave surfaces facing outwardly of the active portion of the devices 500-800 (FIGS. 10-19) when expanded is larger than the radial force exerted by the prior art devices of FIGS. 1A-3D when expanded.

Figure 21:
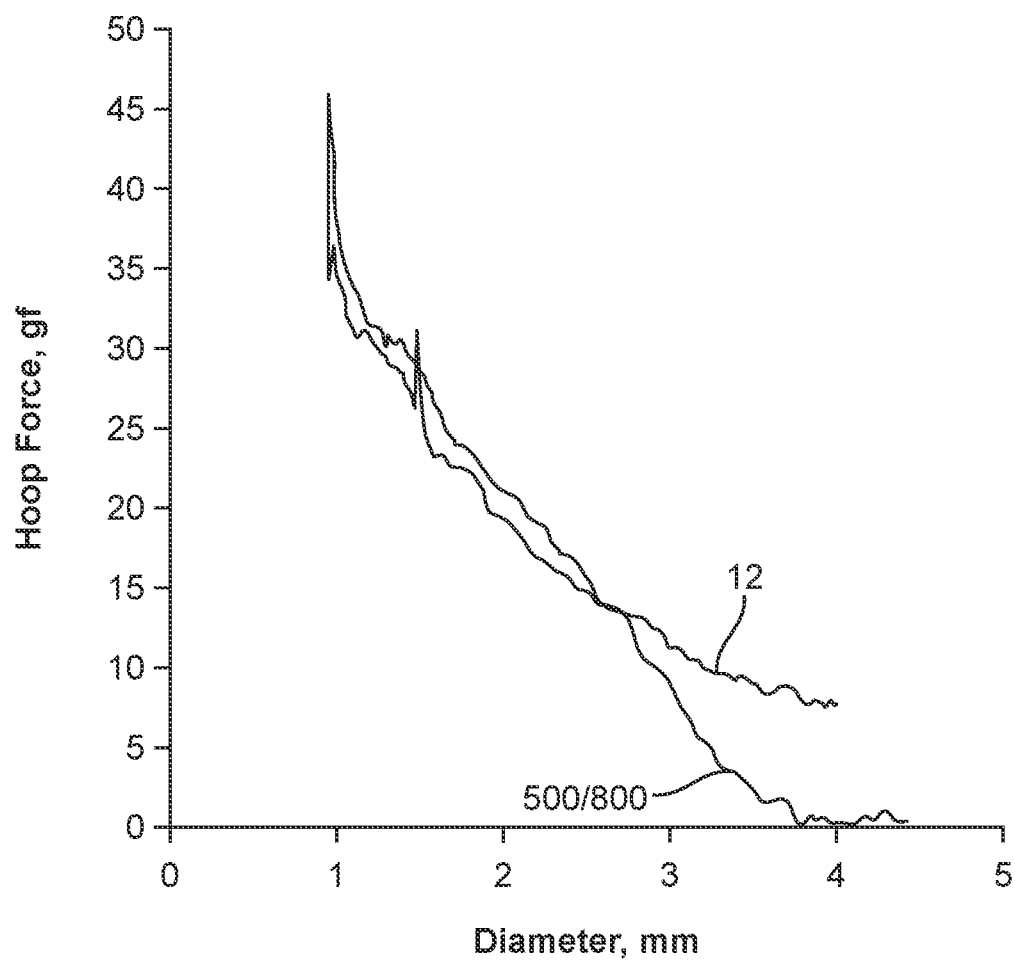
FIG. 21 is table of an overall hoop force of the respective embolectomy devices of FIGS. 10-19 when expanding.

FIG. 21 illustrate an overall hoop force (go of the device 500-800 exerted along the length of the active portion (i.e., sets of arcuate configurations with arcuate concave surfaces facing outwardly) as a function of the diameter in millimeters (mm) of the expandable device 500-800 according to embodiments of the disclose inventions. FIG. 21 illustrates the hoop force of the active portions of the device 500-800 of FIGS. 10-19 as unsheathed (e.g., no longer constrained by catheter/sheath) from 1 mm, expanding diameter into approximately 4.5 mm. Further, FIG. 21 illustrates the hoop force of the prior art device 12 of FIGS. 1-3G as unsheathed from 1 mm, expanding diameter into approximately 4 mm.

Figure 3A:
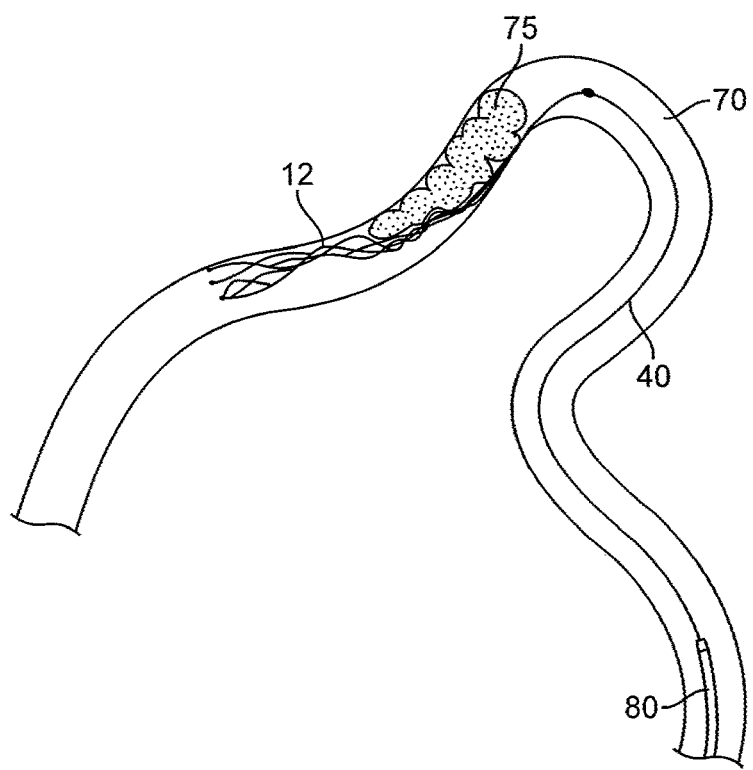
FIGS. 3A-3G are cross-sectional views of the prior art embolectomy device of FIGS. 1A-1B, shown positioned within a blood vessel adjacent to an embolic obstruction.
Figure 3D:
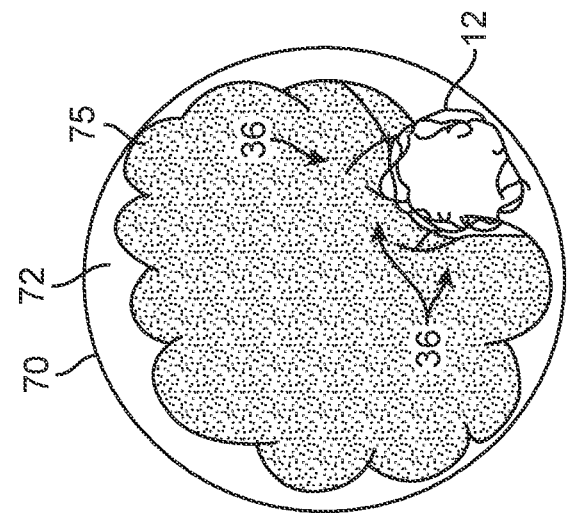
Figure 3C:
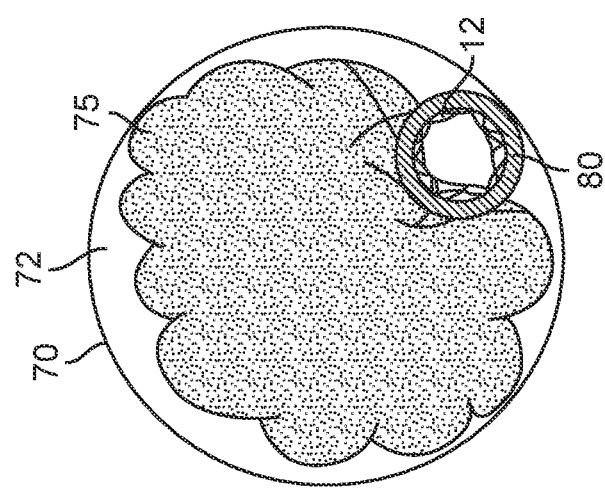
Figure 3B:
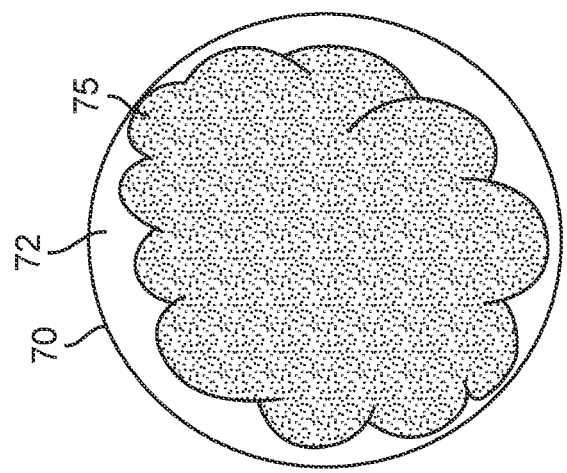
Figure 3G:
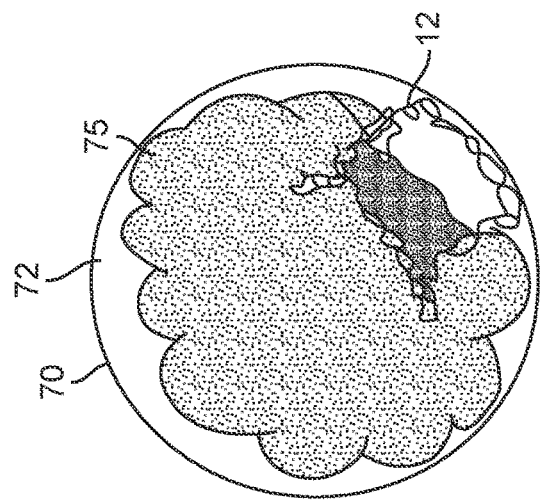
Figure 3F:
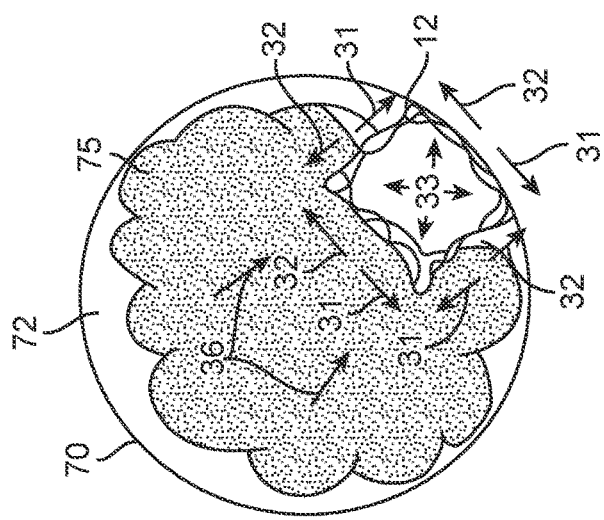
Figure 3E:
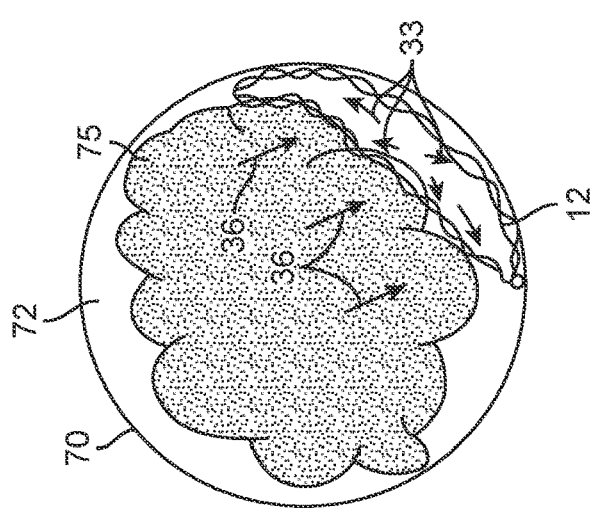

Referring back to FIGS. 20A-D depicting the use of the embolectomy devices 500-800, it should be appreciated that the respective active portions (i.e., the at least three sets of arcuate configurations with arcuate concave surfaces facing outwardly) are configured to engage, snare, integrate, and/or capture the obstruction 75 for removal from the vasculature. As shown in FIGS. 20B-C, when the active portion is no-longer radially constrained by the catheter 80 and begins expansion into their respective "back-to-back" arcuate configuration (i.e., three pairs of "fin-like" configuration), the hoop force 35 (FIG. 21) and/or push forces 31 (FIGS. 22A-D) created during the expansion of the device 500-800, assist to overcome the resistive force 36 of the embolic obstruction 75, allowing for a suitable engagement and/or integration of the device 500-800 with the obstruction 75. One of the advantages of the devices 500-800 is that the "back-to-back" arcuate configuration of the active portion exerts hoop/radial/push forces allowing suitable engagement and/or integration with the obstruction; such "back-to-back" arcuate configuration tends not to create pulling forces that interfere with the expansion of the device, as shown in the prior art devices (FIG. 3F).

In addition to the advantageous configuration of the disclosed devices 500-800 that promotes and/or allows for a more suitable expansion of the device, with resulting engagement and integration with the obstruction, the "back-to-back" arcuate configuration active portions contact the inner surface 71 of the vessel 70 with at least some of their respective maximum/peak regions (e.g., 157/257 of FIGS. 15B-D), as shown in FIGS. 20B-D. The active portion of the device 500-800 is configured to contact the inner surface 71 of the vessel 70 at selected points or regions, as shown in exemplary FIG. 20D where the active portion three pairs of "fin-like" configuration contact the inner surface 71 of the vessel 70 at maximum of six points or regions 71A-F. It should be appreciated that in the use of the active portion of the device 500-800 may contact less than six points or regions of the inner surface 71 of the vessel, as shown for example in FIG. 20C. The selected points or regions 71 of contact (FIGS. 20B-D) between the active portion of the device 500-800 and the inner surface 71 of the vessel 70 allows for less drag or frictional forces when the device 500-800 is withdrawn, compared to the larger drag or frictional forces created between prior art devices (e.g. device 12 of FIGS. 2, 3A, 3D-G) having more surface or area of contact with vessel 70 when the device is withdrawn. The respective maximum/peak regions 157/257 of the active portion of the device 500-800 in contact with the inner surface 71 of the vessel 70 are configured to translate through the vessel 70 in a longitudinal manner creating less drag or frictional forces with the inner surface 71 of the vessel 70.

Figure 2:
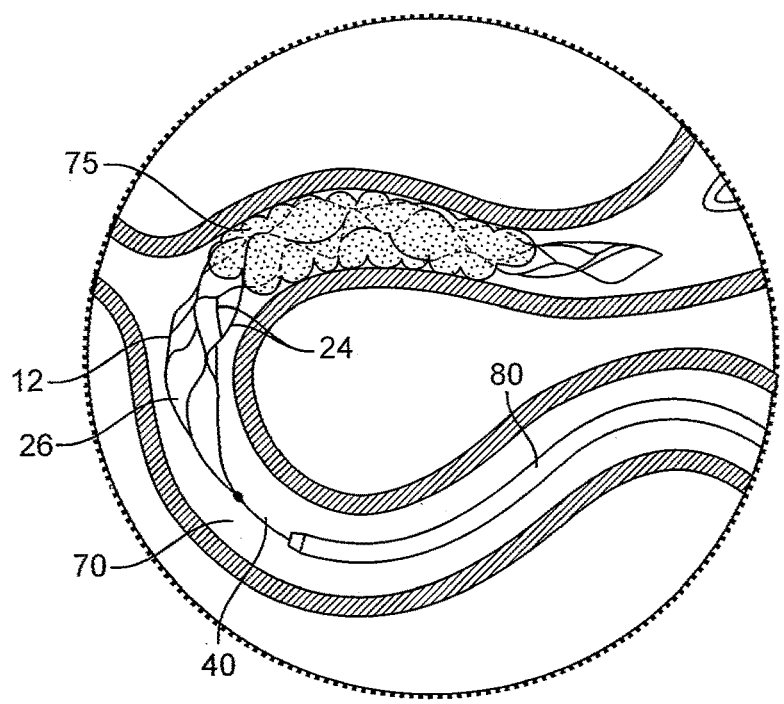
FIG. 2 is a cross-sectional view of the prior art embolectomy device depicted in FIGS. 1A-1B, shown while capturing an embolic obstruction within a blood vessel.
Figure 23A:
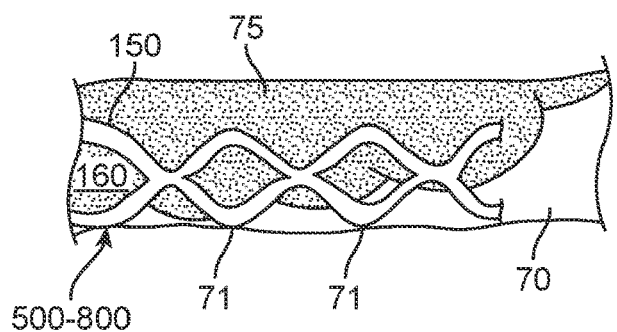
FIGS. 23A-B are respective perspective views of an exemplary detailed portion of any of the respective embolectomy devices of FIGS. 10-19 depicting the integration and retrieval of an embolic obstruction.
Figure 23B:
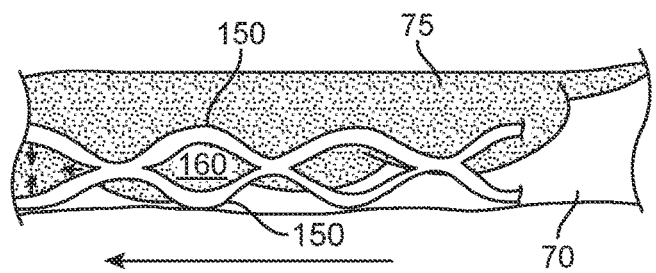

Additionally, the connector 555 disposed in the active portion of the device 500-800 are further configured to increase the mass or contact points between the device 500-800 and the embolic obstruction 75 (FIGS. 20B-D), which are particularly advantageous for engaging, entrapping and retrieving the obstruction 75 when the device 500-800 is withdrawn (FIGS. 23A-B). Thus, another advantage of the devices 500-800 having the "back-to-back" arcuate configuration of the active portion is to provide mass and/or surface of contact (e.g., connector 555, undulating elements 150, elongated elements 250, struts, wires, or the like) within the expanded inner diameter (EID) configured to contact, integrate, entrap and/or engage the obstruction 75 (e.g., FIG. 20D). In contrast, prior art devices (e.g. device 12, FIGS. 1-3G) are configured to expand into a tubular configuration having a lumen, without any or minimal mass or surface of contact in their EID (FIGS. 2, 3F-G)

When the embolectomy devices 500-800 are withdrawn or pulled proximally during the removal of the embolic obstruction from the patient, the advantages of the aforementioned configuration will reduce the likelihood of particles dislodging from the embolic obstruction during its removal. However, in the event that some particles of the embolic obstruction may be dislodged, the operator may use either device 500 or 600 having larger and variable EOD at their respective distal portions 580/680 (FIGS. 10-13C). The distal portions 580/680 of the embolectomy devices 500/600 are configured to engage, retain and/or capture possible dislodged particles for removal. The distal portions 580/680 of the embolectomy devices 500/600 may function as a distal filter by allowing loose embolic particles to be engaged, retained and/or captured for removal when the device 500/600 is withdrawn, while preventing or minimizing the particles to enter the blood stream.

Figure 22A:
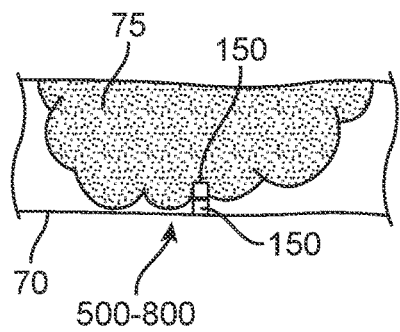
FIGS. 22A-D are respective cross-sectional views of an exemplary detailed portion of any of the respective embolectomy devices of FIGS. 10-19, depicting integration of the device with an embolic obstruction.
Figure 22B:
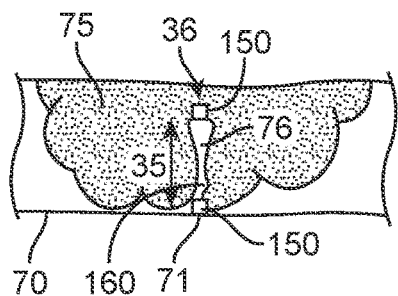
Figure 22C:
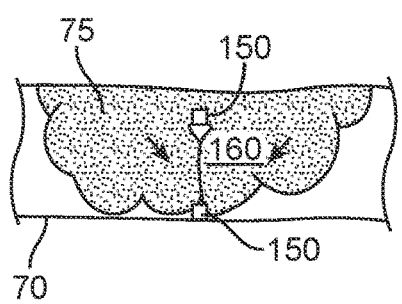
Figure 22D:
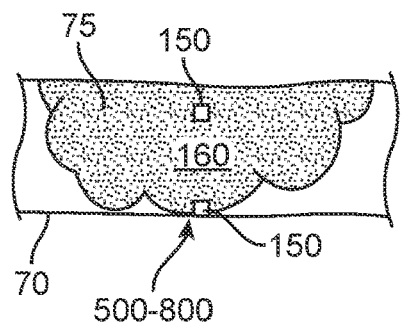

FIGS. 22A-D illustrate cross-sectional views of the interface between a pair of undulating elements 150 forming a cell 160 and the obstruction 75 in a vessel 70, according to the embodiments of the disclosed inventions. For ease in illustration, FIGS. 22A-D depict detailed views of the interface between one pair of undulating elements 150 forming the cell 160 and the obstruction 75. However, it should be appreciated that the interface with the obstruction 75 occurs between several or at least some of the pair of undulating elements 150 or elements 250 during expansion of the active portions of the devices 500-800, as shown in FIGS. 20A-D. FIG. 22A illustrates the cross-sectional views of two undulating elements 150 when the device 500-800 is unsheathed, as previously described. Due to the active portion configuration of the devices 500-800, and/or the previously described "lemon-like" configuration of the two undulating elements 150 exert forces 35 pushing themselves apart in a normal/orthogonal direction and overcoming the obstruction 75 resistive force 36, as shown in FIG. 22B. During the expansion of the device 500-800, one of the undulating element 150 contacts the inner surface 71 of the vessel 70 and the second undulating element 150 pushes through the obstruction 75 defining the cell 160 of the device, while creating a channel 76 in the obstruction 75 (FIG. 22B). After the channel 76 is created, the obstruction 75 herniates into the cell 160 of the device 500-800, closing the channel, as shown in FIG. 22C. Eventually, the obstruction 75 tends to fill the cell 160 (i.e., space between the elements 150) integrating with the device 500-800 (FIG. 20D).

FIGS. 23A-B illustrate perspective views of the interface between a section of the active portion of the device 500-800 and obstruction 75 in a vessel 70, according to the embodiments of the disclosed inventions. For ease in illustration, FIGS. 23A-B depict detailed partial views of the integration between a section of the active portion of the device 500-800 and the obstruction 75. However, it should be appreciated that the integration with the obstruction 75 occurs between several or at least some of the active portion of the device 500-800 during engagement with the obstruction 75 and withdrawal of the device 500-800, as shown in FIGS. 23A-B. FIG. 23A illustrate the device 500-800 contacting the inner surface 71 of the vessel 70 and integrated with the obstruction 75, such as having the obstruction 75 herniating into the cells 160, as previously described (e.g., FIG. 22D). Withdrawal of the device 500-800 creates tension forces drawing the undulating elements 150 closer to each other while reducing the cells 160 volume, which creates pinching and pulling effects on the obstruction 75 that has herniated into the cells 160, as shown in FIG. 23B. As previously described, the configuration of the active portion of the device 500-800 advantageously integrates, engages, capture and/or retrieve obstructions. It should be appreciated that the active portion of the device 500-800 may partially, substantially or completely integrate with obstruction 75. When the device 500-800 engaging, ensnaring or capturing the obstruction 75 is withdrawn, the obstruction 75 would be substantially and/or fully removed from the patient.

It will be appreciated that the embolectomy devices depicted in FIGS. 4-19 may be used in other suitable medical devices, for example, disposed within tubular prosthesis, implants, stents, fluid diverters or the like for both vascular and non-vascular applications. Further, it will be appreciated that combinations of components, features and functions between the embodiments FIGS. 4-19 may be made without departing from the scope of the inventive concepts disclosed herein.

Although particular embodiments have been shown and described herein, it will be understood by those skilled in the art that they are not intended to limit the present inventions, and it will be obvious to those skilled in the art that various changes, permutations, and modifications may be made (e.g., the dimensions of various parts, combinations of parts) without departing from the scope of the disclosed inventions, which is to be defined only by the following claims and their equivalents. The specification and drawings are, accordingly, to be regarded in an illustrative rather than restrictive sense. The various embodiments shown and described herein are intended to cover alternatives, modifications, and equivalents of the disclosed inventions, which may be included within the scope of the appended claims.

The invention claimed is:

1. An elongate embolectomy device biased to transition from a radially constrained configuration to a radially expanded configuration, the embolectomy device comprising:
 a plurality of elongate clot engaging structures, each clot engaging structure comprising a plurality of interconnected struts forming an open cell pattern, and having a proximal active portion and a distal protective portion,
 wherein, when the embolectomy device is in the radially expanded configuration, the active portion of each clot engaging structure has a semi-tubular arcuate profile, including a convex face and a concave face facing opposite the convex face, the clot engaging structures being longitudinally disposed relative to each other such that the concave faces of the active portions are facing radially outward, and
 wherein, when the embolectomy device is in the radially expanded configuration, the protective portion of each clot engaging structure has a semi-tubular arcuate profile, including a convex face and an concave face facing opposite the convex face, wherein the convex faces of the protective portions are facing radially outward, and the concave surfaces of the protective portions are facing radially inward, respectively, relative to the longitudinal axis of the embolectomy device.

2. The embolectomy device of claim 1, wherein a strut of the active portion of a first clot engaging structure is attached to a strut of the active portion of a second clot engaging structure at one or more attachment locations, and wherein the respective protective portions of the first and second clot engaging structures are not attached to one another.

3. The embolectomy device of claim 1, the plurality of clot engaging structures comprising first, second, and third clot engaging structures, wherein a strut of the active portion of the first clot engaging structure is attached to a respective strut of the active portions of the second and third clot engaging structures at one or more attachment locations.

4. The embolectomy device of claim 3, wherein the respective protective portions of the first, second and third clot engaging structures are not attached to one another.

5. The embolectomy device of claim 3, wherein the one or more attachment locations are located on or proximate to the longitudinal axis of the embolectomy device.

6. The embolectomy device of claim 1, wherein struts forming the respective protective portions of the clot engaging structures are coupled at their edges so that the respective protective portions collectively form a trefoil-like barrel shape when the embolectomy device is in the radially expanded configuration.

7. The embolectomy device of claim 1, further comprising a plurality of elongate elements attached to struts of at least one clot engaging structure, the elongate elements comprising one or more of filaments, suture material, fibers, threads, and wires.

8. The embolectomy device of claim 1, further comprising a push wire attached to the active portion of each clot engaging structure, wherein the clot engaging structures are attached to one another at an attachment location in a transition region between the respective active and protective portions of the clot engaging structures.

9. The embolectomy device of claim 1, wherein the protective portion of at least one of the clot engaging structures comprises a distal antenna.

10. The embolectomy device of claim 9, wherein the distal antenna comprises a marker coil and an atraumatic tip.

11. The embolic device of claim 9, wherein the distal antenna comprises at least a portion of a marker coil and of an atraumatic tip.

12. The embolectomy device of claim 1, wherein the active portion of each clot engaging structure imparts a greater radial expansion force than is imparted by the respective protective portion of the clot engaging structure when the embolic device transitions from the radially constrained configuration to the radially expanded configuration.

13. The embolectomy device of any of claim 1, wherein the active portion of each the clot engaging structure has a greater longitudinal length than the respective protective portion of the clot engaging structure when the embolic device is in the radially expanded configuration.

14. The embolectomy device of claim 1, wherein the active portion of each clot engaging structure has a substantially same longitudinal length as the respective protective portion of the clot engaging structure when the embolic device is in the radially expanded configuration.

15. The embolectomy device of claim 1, wherein the active portion of each clot engaging structure comprises an undulating element.

16. The embolectomy device of claim 15, wherein the undulating element defines a valley region and a peak region.

17. The embolectomy device of claim 16, wherein respective undulating elements of adjacent clot engaging structures are coupled to each other at a connection point.

18. The embolectomy device of claim 17, wherein the connection point is between respective valley regions and peak regions of the respective undulating elements.

19. The embolectomy device of claim 15, wherein, when the embolectomy device is transitioning from the radially constrained configuration to the radially expanded configuration, respective undulating elements of the active portions of adjacent elongate clot engaging structures exert a force pushing the respective undulating elements apart from each other.

20. The embolectomy device of claim 19, wherein the embolectomy device is configured such that withdrawing the embolectomy device, in the radially expanded configuration, from a confined space generates a tension force drawing the undulating elements of the active portions of adjacent elongate clot engaging structures closer to each other.

\* \* \* \* \*